US010543131B2

(12) United States Patent
Roe et al.

(10) Patent No.: US 10,543,131 B2
(45) Date of Patent: *Jan. 28, 2020

(54) ABSORBENT ARTICLE WITH LEG CUFFS

(71) Applicant: The Procter & Gamble Company, Cincinnati, OH (US)

(72) Inventors: Donald Carroll Roe, West Chester, OH (US); Jeromy Thomas Raycheck, South Lebanon, OH (US); Abhishek Prakash Surushe, Schwalbach am Taunus (DE); Cornelia Beate Martynus, Nidderau-Ostheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 724 days.

This patent is subject to a terminal disclaimer.

(21) Appl. No.: 15/074,496

(22) Filed: Mar. 18, 2016

(65) Prior Publication Data

US 2016/0270983 A1 Sep. 22, 2016

Related U.S. Application Data

(60) Provisional application No. 62/134,622, filed on Mar. 18, 2015.

(51) Int. Cl.
*A61F 13/15* (2006.01)
*A61F 13/20* (2006.01)
(Continued)

(52) U.S. Cl.
CPC .. *A61F 13/49007* (2013.01); *A61F 13/49011* (2013.01); *A61F 13/49017* (2013.01);
(Continued)

(58) Field of Classification Search
CPC combination set(s) only.
See application file for complete search history.

(56) References Cited

U.S. PATENT DOCUMENTS 3,848,594 A  11/1974 Buell
3,860,003 A  1/1975 Buell
(Continued)

FOREIGN PATENT DOCUMENTS

EP  0 214 636 B1  11/1991
EP  0 404 648 B1  2/1994
(Continued)

OTHER PUBLICATIONS

Search Report and Written Opinion for PCT/US2016/023070 dated Jun. 10, 2016.
(Continued)

*Primary Examiner* — Michele M Kidwell
(74) *Attorney, Agent, or Firm* — Daniel S. Albrecht; William E. Gallagher

(57) ABSTRACT

A disposable absorbent article may include a chassis that includes a topsheet, a backsheet, and an absorbent core disposed between the topsheet and the backsheet; and a leg gasketing system. The leg gasketing system may include an inner cuff and an outer cuff; the inner cuff may include an inner cuff folded edge and an inner cuff material edge and the outer cuff may include an outer cuff folded edge and an outer cuff material edge such that the web of material is folded laterally inward to form the outer cuff folded edge and folded laterally outward to form the inner cuff folded edge. The disposable absorbent article also includes five areas, wherein the first area is more breathable than each of the second area and the third area, and wherein the first area is less breathable than each of the fourth area and the fifth area.

21 Claims, 15 Drawing Sheets

(51) Int. Cl.
*A61F 13/49* (2006.01)
*A61F 13/551* (2006.01)
*A61F 13/53* (2006.01)

(52) U.S. Cl.
CPC ........ *A61F 13/53* (2013.01); *A61F 13/55105* (2013.01); *A61F 2013/49092* (2013.01); *A61F 2013/530481* (2013.01); *A61F 2013/530875* (2013.01)

(56) References Cited

U.S. PATENT DOCUMENTS

| | | |
|---|---|---|
| 4,055,182 A | 10/1977 | Mack |
| 4,324,245 A | 4/1982 | Mesek |
| 4,552,795 A | 11/1985 | Hansen et al. |
| 4,610,678 A | 9/1986 | Weisman et al. |
| 4,639,390 A | 1/1987 | Shoji et al. |
| 4,662,875 A | 5/1987 | Hirotsu et al. |
| 4,673,402 A | 6/1987 | weisman et al. |
| 4,699,622 A | 10/1987 | Toussant et al. |
| 4,738,677 A | 4/1988 | Foreman |
| 4,753,646 A | 6/1988 | Enloe |
| 4,808,178 A | 2/1989 | Aziz et al. |
| 4,808,252 A | 2/1989 | Lash |
| 4,816,025 A | 3/1989 | Foreman |
| 4,834,735 A | 5/1989 | Alemany et al. |
| 4,846,815 A | 7/1989 | Scripps |
| 4,850,990 A | 7/1989 | Huntoon |
| 4,883,549 A | 11/1989 | Frost et al. |
| 4,888,231 A | 12/1989 | Angstadt |
| 4,892,536 A | 1/1990 | Des Marais et al. |
| 4,894,060 A | 1/1990 | Nestegard |
| 4,909,803 A | 3/1990 | Aziz et al. |
| 4,923,660 A | 5/1990 | Willenberg et al. |
| 4,938,755 A | 7/1990 | Foreman |
| 4,946,527 A | 8/1990 | Battrell |
| 4,963,140 A | 10/1990 | Robertson et al. |
| 4,990,147 A | 2/1991 | Freeland |
| 5,021,051 A | 6/1991 | Hiuke |
| 5,026,334 A | 6/1991 | Jeffries |
| 5,026,364 A | 6/1991 | Robertson |
| 5,037,416 A | 8/1991 | Allen et al. |
| 5,061,261 A | 10/1991 | Suzuki et al. |
| 5,137,537 A | 8/1992 | Herron et al. |
| 5,147,345 A | 9/1992 | Young et al. |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,171,391 A | 12/1992 | Chmielewski et al. |
| 5,187,817 A | 2/1993 | Zolner |
| 5,196,000 A | 3/1993 | Clear et al. |
| 5,221,274 A | 6/1993 | Buell et al. |
| 5,242,436 A | 9/1993 | Weil et al. |
| 5,260,345 A | 11/1993 | Des Marais et al. |
| 5,269,775 A | 12/1993 | Freeland et al. |
| 5,281,207 A | 1/1994 | Chmielewski et al. |
| 5,342,338 A | 8/1994 | Roe |
| 5,358,500 A | 10/1994 | LaVon et al. |
| 5,387,207 A | 2/1995 | Dyer et al. |
| 5,397,316 A | 3/1995 | LaVon et al. |
| 5,397,318 A | 3/1995 | Dreier |
| 5,482,625 A | 1/1996 | Kenishi et al. |
| 5,486,418 A | 1/1996 | Ohmory et al. |
| 5,499,978 A | 3/1996 | Buell et al. |
| 5,507,736 A | 4/1996 | Clear et al. |
| 5,531,730 A | 7/1996 | Dreier |
| 5,540,671 A | 7/1996 | Dreier |
| 5,545,158 A | 8/1996 | Jessup |
| 5,554,145 A | 9/1996 | Roe et al. |
| 5,558,660 A | 9/1996 | Dreier |
| 5,558,661 A | 9/1996 | Roe et al. |
| 5,567,254 A | 10/1996 | Sagaser |
| 5,569,227 A | 10/1996 | Vandemoortele et al. |
| 5,569,234 A | 10/1996 | Buell et al. |
| 5,571,096 A | 11/1996 | Dobrin et al. |
| 5,575,785 A | 11/1996 | Gryskiewicz et al. |
| 5,576,090 A | 11/1996 | Suzuki |
| 5,580,411 A | 12/1996 | Nease et al. |
| 5,584,828 A | 12/1996 | Yamamoto et al. |
| 5,591,152 A | 1/1997 | Buell et al. |
| 5,593,401 A | 1/1997 | Sosalla et al. |
| 5,601,543 A | 2/1997 | Dreier et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| 5,643,243 A | 7/1997 | Klemp |
| 5,643,588 A | 7/1997 | Roe et al. |
| 5,694,918 A | 7/1997 | Schleinz |
| 5,672,166 A | 9/1997 | Vandemoortele |
| 5,674,215 A | 10/1997 | Ronnberg |
| 5,681,302 A | 10/1997 | Melbye et al. |
| 5,695,488 A | 12/1997 | Sosalla |
| 5,749,865 A | 5/1998 | Yamamoto et al. |
| 5,769,838 A | 6/1998 | Buell et al. |
| 5,827,259 A | 10/1998 | Laux et al. |
| 5,827,387 A | 10/1998 | Reynolds et al. |
| 5,833,677 A | 11/1998 | Sauer |
| 5,865,823 A | 2/1999 | Curro |
| 5,879,341 A | 3/1999 | Odorzynski et al. |
| 5,895,382 A | 4/1999 | Popp et al. |
| 5,899,895 A | 5/1999 | Robles et al. |
| 5,904,675 A | 5/1999 | Laux et al. |
| 5,911,713 A | 6/1999 | Yamada et al. |
| 5,931,825 A | 8/1999 | Kuen et al. |
| 5,931,826 A | 8/1999 | Faulks et al. |
| 5,938,652 A | 8/1999 | Sauer |
| 5,942,179 A | 8/1999 | Tallentire et al. |
| 5,993,433 A | 11/1999 | St. Louis et al. |
| 6,004,306 A | 12/1999 | Robles et al. |
| 6,107,537 A | 8/2000 | Elder et al. |
| 6,117,121 A | 9/2000 | Faluks et al. |
| 6,120,486 A | 9/2000 | Toyoda et al. |
| 6,120,487 A | 9/2000 | Ashton |
| 6,123,694 A | 9/2000 | Pieniak et al. |
| 6,132,410 A | 10/2000 | Van Gompel et al. |
| 6,135,988 A | 10/2000 | Turner et al. |
| 6,140,551 A | 10/2000 | Niemeyer et al. |
| 6,142,985 A | 11/2000 | Feist |
| 6,152,906 A * | 11/2000 | Faulks et al. ..... A61F 13/49017 604/385.28 |
| 6,171,290 B1 | 1/2001 | Boisse et al. |
| 6,174,302 B1 | 1/2001 | Kumasaka |
| 6,186,996 B1 | 2/2001 | Martin |
| 6,217,563 B1 | 4/2001 | Van Gompel et al. |
| 6,248,097 B1 | 6/2001 | Beitz et al. |
| 6,258,076 B1 | 7/2001 | Glaug et al. |
| 6,264,639 B1 | 7/2001 | Sauer |
| 6,264,641 B1 | 7/2001 | Van Gompel et al. |
| 6,264,642 B1 | 7/2001 | Kuen et al. |
| 6,264,643 B1 | 7/2001 | Toyoda et al. |
| 6,280,426 B1 | 8/2001 | Turner et al. |
| 6,293,934 B1 | 9/2001 | Kumasaka |
| 6,312,420 B1 | 11/2001 | Sasaki et al. |
| 6,315,764 B1 | 11/2001 | Faulks et al. |
| 6,336,922 B1 | 1/2002 | Van Gompel et al. |
| 6,346,162 B1 | 2/2002 | Reynolds et al. |
| 6,364,863 B1 | 4/2002 | Yamamoto et al. |
| 6,375,646 B1 | 4/2002 | Widlund et al. |
| 6,413,249 B1 | 7/2002 | Turi et al. |
| 6,425,889 B1 | 7/2002 | Kitaoka et al. |
| 6,432,098 B1 | 8/2002 | Kline et al. |
| 6,436,216 B1 | 8/2002 | Grover |
| 6,440,117 B1 | 8/2002 | Itoh et al. |
| 6,440,239 B1 | 8/2002 | Vogt |
| 6,451,001 B2 | 9/2002 | Kumasaka |
| 6,461,342 B1 | 10/2002 | Tanji et al. |
| 6,478,785 B1 | 11/2002 | Ashton et al. |
| 6,491,677 B1 | 12/2002 | Glaug et al. |
| 6,494,872 B1 | 12/2002 | Suzuki et al. |
| 6,506,185 B1 | 1/2003 | Sauer et al. |
| 6,527,893 B1 | 3/2003 | Boisse et al. |
| 6,562,123 B2 | 4/2003 | Katayama et al. |

(56) References Cited

U.S. PATENT DOCUMENTS

| | | |
|---|---|---|
| 6,569,139 B1 | 5/2003 | Datta et al. |
| 6,569,140 B1 | 5/2003 | Mizutani et al. |
| 6,565,976 B1 | 7/2003 | Jitoe et al. |
| 6,592,562 B2 | 7/2003 | Menard et al. |
| 6,613,033 B1 | 9/2003 | Popp et al. |
| 6,629,967 B1 | 10/2003 | Simmons et al. |
| 6,638,262 B2 | 10/2003 | Suzuki et al. |
| 6,641,570 B2 | 11/2003 | Mishima et al. |
| 6,641,692 B2 | 11/2003 | Reynolds et al. |
| 6,659,990 B1 | 12/2003 | Odorzynski et al. |
| 6,682,515 B1 | 1/2004 | Mizutani et al. |
| 6,682,516 B2 | 1/2004 | Johnston et al. |
| 6,699,228 B1 | 3/2004 | Chmielewski et al. |
| 6,702,801 B2 | 3/2004 | Van Gompel et al. |
| 6,706,029 B1 | 3/2004 | Suzuki et al. |
| 6,706,030 B1 | 3/2004 | Okuda et al. |
| 6,767,343 B2 | 7/2004 | Shimada et al. |
| 6,767,344 B2 | 7/2004 | Suzuki |
| 6,808,582 B2 | 10/2004 | Popp et al. |
| 6,837,958 B2 | 1/2005 | Otsubo et al. |
| 6,840,930 B1 | 1/2005 | Miyamoto et al. |
| 6,884,310 B2 | 4/2005 | Roessler et al. |
| 6,903,793 B2 | 6/2005 | Ukegawa et al. |
| 6,921,394 B2 | 7/2005 | Yasushi et al. |
| 6,978,486 B2 | 12/2005 | Zhou et al. |
| 7,014,632 B2 | 3/2006 | Takino et al. |
| 7,018,368 B2 | 3/2006 | Van Gompel et al. |
| 7,037,300 B2 | 5/2006 | Kling |
| 7,135,014 B2 | 11/2006 | Sasaki et al. |
| 7,150,729 B2 | 12/2006 | Shimada et al. |
| 7,156,828 B2 | 1/2007 | Ostrow |
| 7,163,530 B1 | 1/2007 | Toyoshima et al. |
| 7,169,136 B2 | 1/2007 | Otsubo et al. |
| 7,189,219 B1 | 3/2007 | Kasai et al. |
| 7,195,621 B2 | 3/2007 | Ohnishi et al. |
| 7,207,978 B2 | 4/2007 | Takino et al. |
| 7,226,437 B2 | 6/2007 | Sasaki et al. |
| 7,264,686 B2 | 9/2007 | Thorson et al. |
| 7,291,138 B2 | 11/2007 | Hoshino et al. |
| 7,331,946 B2 | 2/2008 | Shimada et al. |
| 7,338,479 B2 | 3/2008 | Fujioka et al. |
| 7,378,360 B2 | 5/2008 | Clark et al. |
| 7,435,243 B2 | 10/2008 | Miyamoto |
| 7,435,244 B2 | 10/2008 | Schroer et al. |
| 7,527,616 B2 | 5/2009 | Miyamoto |
| 7,561,602 B1 | 7/2009 | Nakabayashi |
| 7,569,039 B2 | 8/2009 | Matsuda et al. |
| 7,604,625 B2 | 10/2009 | Turi et al. |
| 7,621,900 B2 | 11/2009 | Van Gompel et al. |
| 7,626,073 B2 | 12/2009 | Catalan |
| 7,666,176 B2 | 2/2010 | Erdman et al. |
| 7,670,325 B2 | 3/2010 | Sugiyama et al. |
| 7,708,725 B2 | 5/2010 | Kinoshita et al. |
| 7,722,590 B2 | 5/2010 | Tsuji et al. |
| 7,722,591 B2 | 5/2010 | Back |
| 7,727,214 B2 | 6/2010 | Torigoshi et al. |
| 7,727,215 B2 | 6/2010 | Kenmochi et al. |
| 7,744,576 B2 | 6/2010 | Busam et al. |
| 7,744,579 B2 | 6/2010 | Langdon et al. |
| 7,750,203 B2 | 7/2010 | Becker et al. |
| 7,753,899 B2 | 7/2010 | Mori et al. |
| 7,754,040 B2 | 7/2010 | Norrby |
| 7,785,309 B2 | 8/2010 | Van Gompel et al. |
| 7,794,441 B2 | 9/2010 | Ashton et al. |
| 7,834,236 B2 | 11/2010 | Middlesworth et al. |
| 7,838,724 B2 | 11/2010 | Van Gompel et al. |
| 7,879,017 B1 | 2/2011 | Tabata et al. |
| 7,918,839 B2 | 4/2011 | Ehrnsperger et al. |
| 7,918,840 B2 | 4/2011 | Corneliusson |
| 7,959,619 B2 | 6/2011 | Cartier et al. |
| 8,002,760 B2 | 8/2011 | Ehrnsperger et al. |
| 8,038,662 B2 | 10/2011 | Hornung et al. |
| 8,043,274 B2 | 10/2011 | Milnar et al. |
| 8,043,275 B2 | 10/2011 | Peterson |
| 8,062,279 B2 | 11/2011 | Miyamoto |
| 8,075,543 B2 | 12/2011 | Okuda |
| 8,105,303 B2 | 1/2012 | Sakaguchi |
| 8,114,059 B2 | 2/2012 | Ehrnsperger et al. |
| 8,152,788 B2 | 4/2012 | Beckert et al. |
| 8,182,627 B2 | 5/2012 | Eckstein et al. |
| 8,211,077 B2 | 7/2012 | Sugiyama et al. |
| 8,212,102 B2 | 7/2012 | Kumasaka |
| 8,231,592 B2 | 7/2012 | Suzuki et al. |
| 8,251,967 B2 | 8/2012 | Malowaniec et al. |
| 8,328,782 B2 | 12/2012 | Catalan et al. |
| 8,333,749 B2 | 12/2012 | Tsang et al. |
| 8,348,919 B2 | 1/2013 | Langdon et al. |
| 8,353,891 B2 | 1/2013 | Hornung et al. |
| 8,377,023 B2 | 2/2013 | Sawyer et al. |
| 8,382,735 B2 | 2/2013 | Torigoshi et al. |
| 8,475,424 B2 | 7/2013 | Fujimoto et al. |
| 8,496,638 B2 | 7/2013 | Lord et al. |
| 8,513,483 B2 | 8/2013 | Tee et al. |
| 8,518,010 B2 | 8/2013 | Kuwano et al. |
| 8,551,064 B2 | 10/2013 | LaVon et al. |
| 8,568,566 B2 | 10/2013 | Jackels et al. |
| 8,663,184 B2 | 3/2014 | Liu et al. |
| 8,668,680 B2 | 3/2014 | Ichikawa et al. |
| 8,679,084 B2 | 3/2014 | Kurihara |
| 8,716,549 B2 | 5/2014 | Cheng et al. |
| 8,764,722 B2 | 7/2014 | Rhei et al. |
| 8,777,918 B2 | 7/2014 | Kuwano et al. |
| 8,795,250 B2 | 8/2014 | O'Connell |
| 8,939,957 B2 | 1/2015 | Raycheck et al. |
| 9,044,358 B2 | 6/2015 | Nakajima et al. |
| 9,066,838 B2 | 6/2015 | Hippe et al. |
| 9,089,455 B2 | 7/2015 | Raycheck et al. |
| 9,750,651 B2 | 9/2017 | Bianchi et al. |
| 10,022,280 B2 | 7/2018 | Ehrnsperger et al. |
| 2002/0128626 A1 | 9/2002 | Friderich et al. |
| 2002/0177829 A1 | 11/2002 | Fell et al. |
| 2003/0023220 A1 | 1/2003 | Ukegawa et al. |
| 2003/0050616 A1 | 3/2003 | Reynolds et al. |
| 2003/0135185 A1 | 7/2003 | Crowther |
| 2004/0002690 A1 | 1/2004 | Miyamoto |
| 2004/0127876 A1 | 7/2004 | Stevens |
| 2004/0129597 A1 | 7/2004 | Guzmann et al. |
| 2004/0158217 A1 | 8/2004 | Wu et al. |
| 2004/0222553 A1 | 11/2004 | Desai et al. |
| 2004/0243085 A1 | 12/2004 | Veith et al. |
| 2005/0003048 A1 | 1/2005 | Pearce et al. |
| 2005/0004549 A1 | 1/2005 | Maas et al. |
| 2005/0095700 A1 | 5/2005 | Budzowski et al. |
| 2005/0113790 A1 | 5/2005 | Suzuki |
| 2005/0177123 A1 | 8/2005 | Catalan |
| 2005/0203479 A1 | 9/2005 | Sakaguchi et al. |
| 2005/0215155 A1 | 9/2005 | Young et al. |
| 2005/0222550 A1 | 10/2005 | Mitsui et al. |
| 2005/0281757 A1 | 12/2005 | Ibrahim et al. |
| 2005/0288645 A1 | 12/2005 | LaVon |
| 2006/0014460 A1 | 1/2006 | Isele et al. |
| 2006/0058767 A1 | 3/2006 | Zhang et al. |
| 2006/0058768 A1 | 3/2006 | Zhang et al. |
| 2006/0111686 A1 | 5/2006 | Schneider |
| 2006/0264860 A1 | 11/2006 | Beck et al. |
| 2006/0270302 A1 | 11/2006 | Ando et al. |
| 2007/0005040 A1 | 1/2007 | Langdon et al. |
| 2007/0088116 A1 | 4/2007 | Abba et al. |
| 2007/0123834 A1 | 5/2007 | McDowall et al. |
| 2007/0191808 A1 | 8/2007 | Toyoshima et al. |
| 2007/0287980 A1 | 12/2007 | Kline et al. |
| 2007/0287983 A1 | 12/2007 | Lodge et al. |
| 2008/0077111 A1 | 3/2008 | Erdman et al. |
| 2008/0195070 A1 | 8/2008 | Ponomarenko et al. |
| 2008/0195071 A1 | 8/2008 | Ponomarenko et al. |
| 2008/0312617 A1 | 12/2008 | Hundorf et al. |
| 2008/0312631 A1 | 12/2008 | Okuda |
| 2009/0118689 A1 | 5/2009 | Lawson et al. |
| 2009/0157034 A1 | 6/2009 | Mattingly et al. |
| 2009/0195187 A1 | 6/2009 | Ashraf |
| 2009/0182298 A1 | 7/2009 | Kumasaka |
| 2009/0275911 A1 | 11/2009 | Hornung et al. |
| 2009/0312730 A1 | 12/2009 | LaVon et al. |
| 2009/0312734 A1 | 12/2009 | LaVon et al. |

(56) References Cited

U.S. PATENT DOCUMENTS

| | | |
|---|---|---|
| 2010/0028638 A1 | 2/2010 | Reichardt et al. |
| 2010/0193110 A1 | 8/2010 | Eckstein et al. |
| 2010/0305532 A1 | 12/2010 | Ashton et al. |
| 2010/0312214 A1 | 12/2010 | Shimada et al. |
| 2010/0318054 A1 | 12/2010 | Langdon et al. |
| 2011/0004177 A1 | 1/2011 | Roe et al. |
| 2011/0022019 A1 | 1/2011 | Shimada et al. |
| 2011/0066128 A1 | 3/2011 | Takahashi |
| 2011/0092944 A1 | 4/2011 | Sagasaka et al. |
| 2011/0172626 A1 | 7/2011 | Misumo et al. |
| 2011/0178489 A1 | 7/2011 | Baba et al. |
| 2011/0196327 A1 | 8/2011 | Chhabra et al. |
| 2011/0223381 A1 | 9/2011 | Sauter et al. |
| 2011/0245792 A1 | 10/2011 | O'Connell |
| 2011/0250256 A1 | 10/2011 | Hyun-Oh et al. |
| 2012/0027702 A1 | 2/2012 | Bernoud et al. |
| 2012/0073760 A1 | 3/2012 | Hamada et al. |
| 2012/0277702 A1 | 11/2012 | Raycheck et al. |
| 2012/0277713 A1 | 11/2012 | Raycheck et al. |
| 2012/0289921 A1 | 11/2012 | Hashino et al. |
| 2012/0316526 A1 | 12/2012 | Jackels et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2012/0330262 A1 | 12/2012 | Lawson et al. |
| 2012/0330263 A1 | 12/2012 | Lawson et al. |
| 2012/0330264 A1 | 12/2012 | Lawson et al. |
| 2013/0041340 A1 | 2/2013 | Kawakami et al. |
| 2013/0255865 A1 | 10/2013 | Brown et al. |
| 2014/0005621 A1 | 1/2014 | Roe et al. |
| 2014/0142529 A1 | 5/2014 | Cheng |
| 2014/0163511 A1 | 6/2014 | Roe et al. |
| 2015/0073372 A1 | 3/2015 | Hippe et al. |
| 2016/0067940 A1 | 3/2016 | Liebe et al. |
| 2016/0270971 A1* | 9/2016 | Raycheck ......... A61F 13/49007 |
| 2016/0270972 A1* | 9/2016 | Surushe ............ A61F 13/49007 |
| 2016/0270973 A1* | 9/2016 | Surushe ............ A61F 13/49007 |
| 2016/0270974 A1* | 9/2016 | Surushe ............ A61F 13/49007 |
| 2016/0270975 A1* | 9/2016 | Surushe ............ A61F 13/49007 |
| 2016/0270977 A1 | 9/2016 | Surushe et al. |
| 2016/0270978 A1* | 9/2016 | Raycheck ......... A61F 13/55105 |
| 2016/0270979 A1* | 9/2016 | Raycheck ......... A61F 13/49009 |
| 2016/0270980 A1* | 9/2016 | Raycheck ......... A61F 13/49011 |
| 2016/0270981 A1* | 9/2016 | Raycheck ......... A61F 13/49011 |
| 2016/0270982 A1* | 9/2016 | Raycheck ......... A61F 13/49007 |
| 2016/0270983 A1* | 9/2016 | Roe ................... A61F 13/49007 |
| 2016/0270985 A1* | 9/2016 | Raycheck ......... A61F 13/49001 |
| 2016/0287449 A1 | 10/2016 | Surushe et al. |
| 2017/0266062 A1 | 9/2017 | Raycheck et al. |

FOREIGN PATENT DOCUMENTS

| | | | |
|---|---|---|---|
| EP | 0 412 579 B1 | 6/1994 | |
| EP | 0 403 832 B1 | 10/1994 | |
| EP | 0 773 769 B1 | 11/2000 | |
| EP | 0 866 682 B1 | 3/2002 | |
| EP | 0 376 022 B2 | 3/2006 | |
| EP | 1 905 402 A2 | 6/2008 | |
| JP | 6426701 A | 1/1989 | |
| JP | H0265861 A | 3/1990 | |
| JP | 5192367 B2 | 8/1993 | |
| JP | 7184955 A | 7/1995 | |
| JP | 07-313550 A | 12/1995 | |
| JP | H08-215239 A | 8/1996 | |
| JP | 8252280 A | 10/1996 | |
| JP | 2525656 | 2/1997 | |
| JP | 9215709 A | 8/1997 | |
| JP | 2810738 B2 | 10/1998 | |
| JP | H10-277091 A | 10/1998 | |
| JP | 11253483 A | 9/1999 | |
| JP | 11318978 A | 11/1999 | |
| JP | 11323611 A | 11/1999 | |
| JP | 2602070 Y2 | 12/1999 | |
| JP | 2000-014702 A | 1/2000 | |
| JP | 2603259 Y2 | 3/2000 | |
| JP | 2000-254176 A | 9/2000 | |
| JP | 2000-288016 A | 10/2000 | |
| JP | 2000-342623 A | 12/2000 | |
| JP | 2001-245922 A | 9/2001 | |
| JP | 3242586 B2 | 12/2001 | |
| JP | 2002-102279 A | 4/2002 | |
| JP | 2002-209938 A | 7/2002 | |
| JP | 3315993 B2 | 8/2002 | |
| JP | 2002-253604 A | 9/2002 | |
| JP | 3391776 B2 | 3/2003 | |
| JP | 3391779 B2 | 3/2003 | |
| JP | 3406231 B2 | 5/2003 | |
| JP | 3488506 B2 | 1/2004 | |
| JP | 3605426 B2 | 1/2004 | |
| JP | 3493211 B2 | 2/2004 | |
| JP | 2014-083191 A | 5/2004 | |
| JP | 3592591 B2 | 11/2004 | |
| JP | 3606297 | 1/2005 | |
| JP | 3615894 B2 | 8/2005 | |
| JP | 3771466 B2 | 4/2006 | |
| JP | 3773550 B2 | 5/2006 | |
| JP | 3825977 B2 | 9/2006 | |
| JP | 2006-263306 A | 10/2006 | |
| JP | 2006-320709 A | 11/2006 | |
| JP | 3856904 B2 | 12/2006 | |
| JP | 3884292 B2 | 2/2007 | |
| JP | 2007-143633 A | 6/2007 | |
| JP | 3926585 B2 | 6/2007 | |
| JP | 3953228 B2 | 8/2007 | |
| JP | 2008-302138 A | 12/2008 | |
| JP | 4215370 B2 | 1/2009 | |
| JP | 2009-056142 A | 3/2009 | |
| JP | 4330281 B2 | 9/2009 | |
| JP | 4996508 B2 | 8/2012 | |
| JP | 5001756 B2 | 8/2012 | |
| JP | 2014-012219 A | 1/2014 | |
| JP | 2014-068848 A | 4/2014 | |
| JP | 5651801 B1 | 1/2015 | |
| WO | WO 1994-04656 A2 | 3/1994 | |
| WO | WO 1993-03698 A1 | 6/1994 | |
| WO | WO 1995-16746 A1 | 6/1995 | |
| WO | WO 1996-03953 A1 | 2/1996 | |
| WO | WO 1997-20532 A1 | 6/1997 | |
| WO | WO 2002-36059 A1 | 5/2002 | |
| WO | WO 2006-135357 A1 | 12/2006 | |
| WO | WO 2013-065618 A1 | 5/2013 | |
| WO | WO 2013-065619 A1 | 5/2013 | |
| WO | WO 2014-147879 A1 | 9/2014 | |
| WO | WO 2015-005166 A1 | 1/2015 | |
| WO | WO 2015-198928 A1 | 12/2015 | |
| WO | WO 2016-051936 A1 | 4/2016 | |
| WO | WO 2016-051937 A1 | 4/2016 | |
| WO | WO 2016-051938 A1 | 4/2016 | |

OTHER PUBLICATIONS

Search Report and Written Opinion for PCT/US2016/023072 dated Jun. 8, 2016.
Search Report and Written Opinion for PCT/US2016/023074 dated Jun. 24, 2016.
Search Report and Written Opinion for PCT/US2016/023078 dated Jun. 30, 2016.
Search Report and Written Opinion for PCT/US2016/023080 dated Jun. 13, 2016.
Search Report and Written Opinion for PCT/US2016/023082 dated Jun. 22, 2016.
Search Report and Written Opinion for PCT/US2016/023084 dated Jun. 21, 2016.
Search Report and Written Opinion for PCT/US2016/023087 dated Jun. 30, 2016.
Search Report and Written Opinion for PCT/US2016/023088 dated Jun. 30, 2016.
All Office Actions for U.S. Appl. No. 15/074,453.
All Office Actions for U.S. Appl. No. 15/074,543.
All Office Actions for U.S. Appl. No. 15/074,583.
All Office Actions for U.S. Appl. No. 15/074,650.

(56) References Cited

OTHER PUBLICATIONS

All Office Actions for U.S. Appl. No. 15/074,675.
PCT International Search Report, dated Jul. 5, 2016 (12 pages).
All Office Actions for U.S. Appl. No. 15/074,047.
All Office Actions for U.S. Appl. No. 15/074,066.
All Office Actions for U.S. Appl. No. 15/074,108.
All Office Actions for U.S. Appl. No. 15/074,145.
All Office Actions for U.S. Appl. No. 15/074,211.
All Office Actions for U.S. Appl. No. 15/074,240.
All Office Actions for U.S. Appl. No. 15/074,300.
All Office Actions for U.S. Appl. No. 15/074,352.
All Office Actions for U.S. Appl. No. 15/074,382.
U.S. Appl. No. 15/074,543, filed Mar. 18, 2016, Jeromy Thomas Raycheck et al.

* cited by examiner

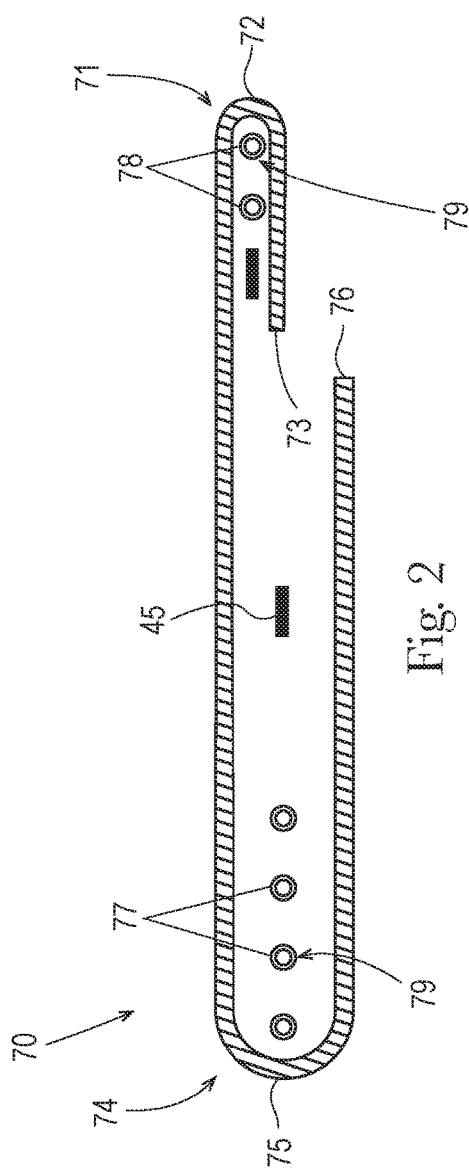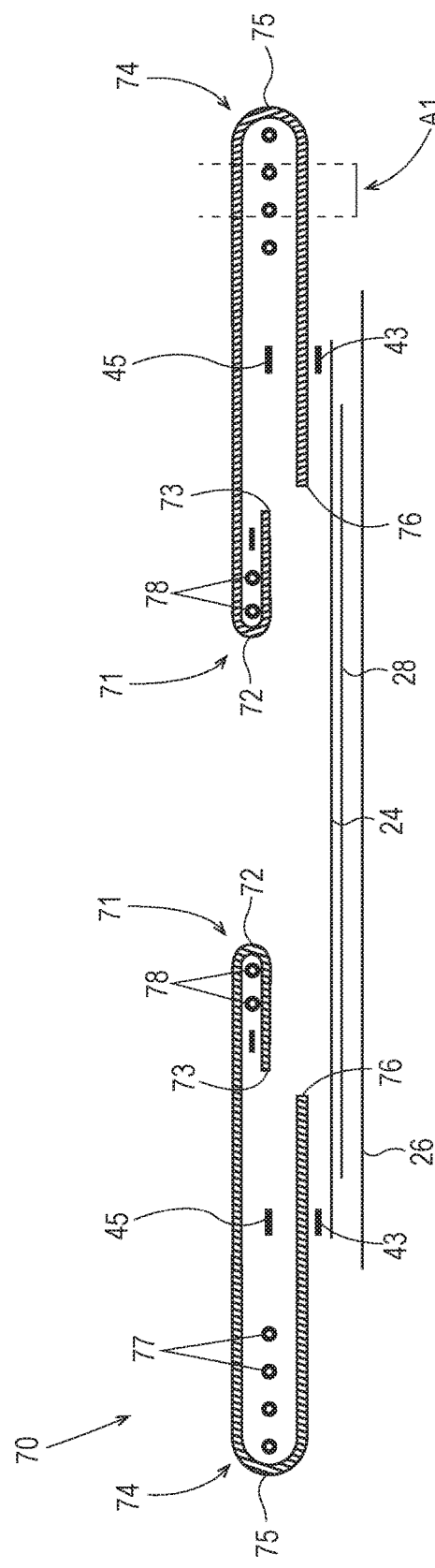

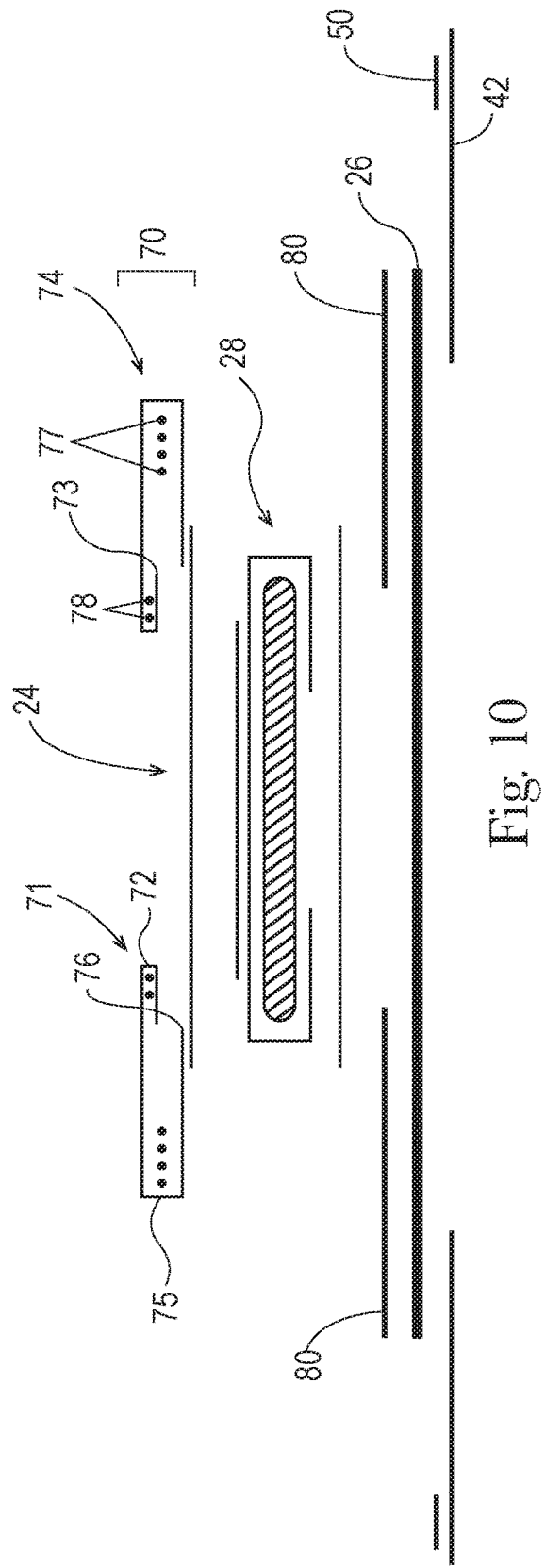

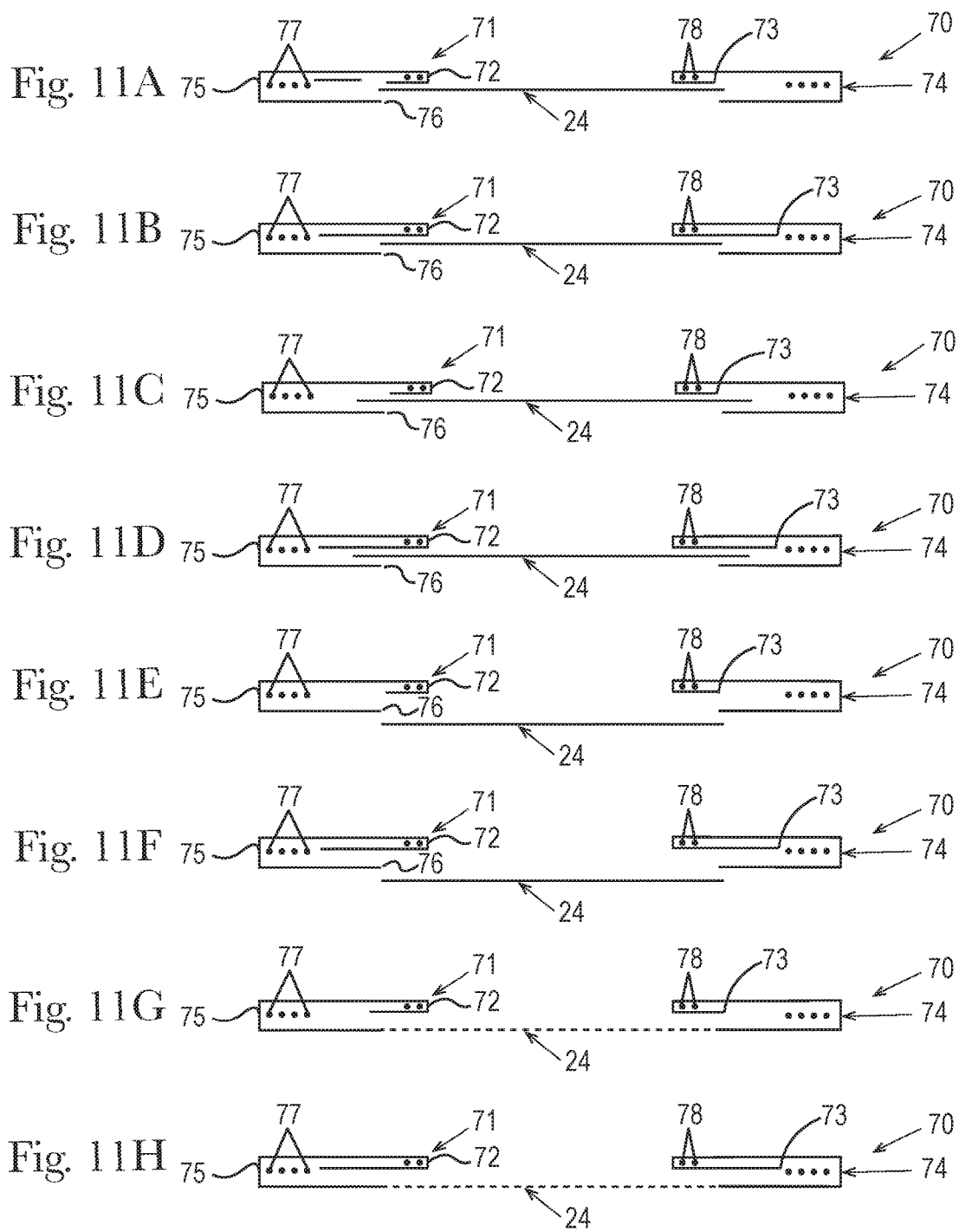

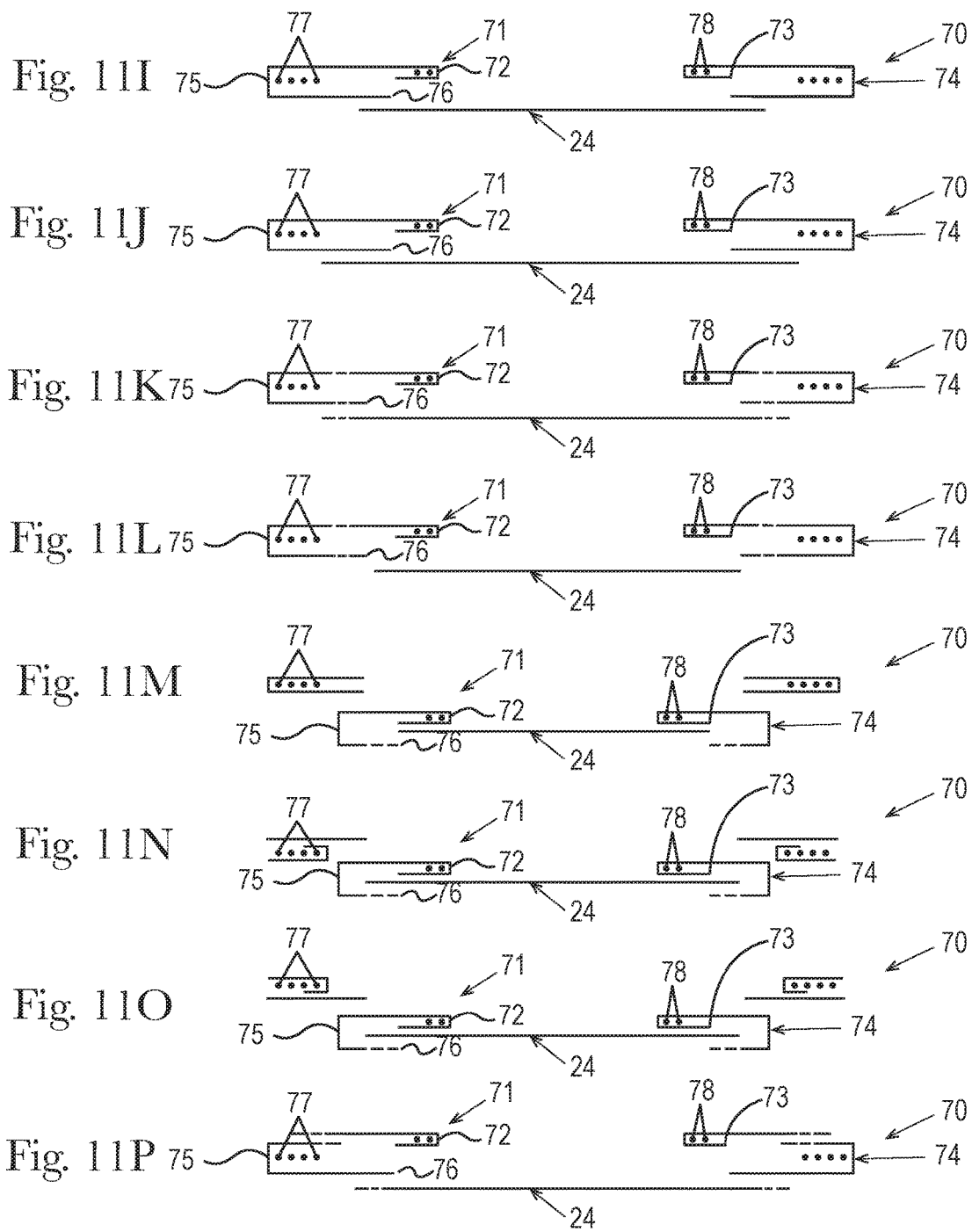

ABSORBENT ARTICLE WITH LEG CUFFS

CROSS REFERENCE TO RELATED APPLICATION

This application claims the benefit of U.S. Provisional Application No. 62/134,622 filed Mar. 18, 2015, the substance of which is incorporated herein by reference.

FIELD OF INVENTION

This invention relates to absorbent articles (e.g., diapers, adult incontinence articles, feminine hygiene pads) having improved leg cuffs that yield a more garment-like article, as well as having improved functional characteristics (e.g., reduced leakage, fecal material containment).

BACKGROUND OF THE INVENTION

It has long been known that absorbent articles such as conventional absorbent articles (e.g., diapers, adult incontinence articles, feminine hygiene pads) offer the benefit of receiving and containing urine and/or other bodily exudates (e.g., feces, menses, mixture of feces and urine, mixture of menses and urine, etc.). To effectively contain bodily exudates, the article should provide a snug fit around the waist and legs of a wearer.

Current diaper designs frequently include the use of a barrier leg cuff to prevent leakage of bodily exudates and an outer cuff which provides a covering over the barrier leg cuff to minimize the visibility of exudates through the barrier cuff and provide a secondary means to capture bodily exudates should they breach the barrier leg cuff. The barrier leg cuff may be made using a hydrophobic nonwoven and may be disposed on the body-facing surface of the absorbent article or connected to the body-facing surface of the film backsheet layer. The barrier leg cuff may be a substantially liquid impervious layer that prevents bodily exudates from passing out of the sides of the article and may also be highly breathable, allowing outside air to reach the skin to help maintain a healthy level of skin hydration. In many current diapers, the outer cuff comprises the polymeric film layer of the backsheet to provide high opacity required to cover the barrier leg cuff as well as to prevent molten adhesive from passing through the cuff to the garment-facing surface of the article during manufacturing. The outer cuff contains the outer leg elastic strands, which create the contraction forces and gathers, and can be sandwiched between the cuff material and backsheet material. The elastic strands in the leg cuffs are typically joined with molten adhesive during manufacture, and the hot adhesive generally has the potential to pass through nonwoven materials during manufacture, causing contamination of manufacturing lines as well as the potential for stickiness on the outside surface of the article. The polymeric film generally is used to prevent these issues, however, results in a plastic-like look as well as a noisy application process, and can also be an impediment to breathability, leading to diaper rash and/or anhidrosis.

Because of manufacturing tolerances when cutting, tracking, and combining materials, the outer leg elastic strands are generally spaced inboard from the longitudinal edge of the article in the crotch region. This prevents inadvertent cutting or exposure of the outer leg elastic strands during the manufacturing process. This design does not result in the outermost portion of the longitudinal edge of the product continuously contacting closely to the skin of the user during wear. Thus, the ability of the elastic strand(s) to control the edge of the article diminishes as the distance between the outermost elastic and the edge increases, leading to a more random distribution of larger gathers which contact the skin at larger intervals or sometimes not at all. This effect can lead to user perception that the diaper may leak where the longitudinal edge does not contact the skin of the user. In addition, many articles currently available contain only two to three outer leg elastics per side to create the gathers, increasing the difficulty of achieving the desired appearance of a wide finished leg cuff or more garment-like cuff such as the elasticized hemmed edge of the arm cuff of a sweater. If the elastics are spaced more closely, the result is a narrow section of elasticized zone, which results in a less finished, less comfortable, and less clothing-like appearance. If the elastics are spaced farther apart, the gathers can appear to separate further from the skin of the user, leading to a perception of potential leakage risk. As discussed above, this is driven by having less control of the gathers between strands of increasing separation.

Accordingly, it is desirable to provide an absorbent article with a folded outer cuff design having finished edges with elastics that are close to the edge to maintain a close proximity to the skin to create improved fit, a more aesthetically pleasing, clothing-like design and improved leakage protection.

However, even with the improved leakage protection provided by the cuff designs detailed herein, the most common mode of failure for absorbent articles still occurs when body exudates leak out of the gaps between the article and the wearer's legs and/or waist. When fecal material (e.g., runny bowel movement, a mixture of bowel movement and urine, etc.) is not absorbed into the topsheet and core of absorbent article, the fecal material can leak out of the gaps between the article and the wearer's legs or waist. In situations where a wearer exudes a higher quantity of fecal material—which is absorbed by the absorbent core more slowly than urine—the fecal material may move laterally along the body-side surface of the absorbent article and reach the barrier leg cuff. After the fecal material reaches the barrier leg cuffs, it may travel longitudinally along the barrier leg cuffs. Due to the movement of the wearer and/or a shortage of available space under the barrier cuffs and/or within the absorbent article, the fecal material may leak out of the gaps between the article and the wearer's legs and/or waist. This results in soiling, wetting, or otherwise contaminating the wearer's clothing or other articles (e.g., bedding, furniture, caregiver clothing, etc.) that come in contact with the wearer's leaky absorbent article.

Accordingly, it is of continued interest to provide an economically viable disposable absorbent article with the ability to minimize the negative effects of bodily extrudate leaks, while also making it easier to clean the wearer when the soiled disposable absorbent article is removed. To that end, it is of continued interest to provide a disposable absorbent article having sufficient retention capability to safely and cleanly retain bodily extrudate away from the wearer's clothing and/or skin throughout the expected time of article use. Further, it is also of continued interest to provide an economically viable disposable absorbent article with the previously mentioned features, along with higher breathability in appropriate regions of the absorbent article to lessen cases of wearer diaper rash and/or anhidrosis, with higher breathability leading to better skin health of the areas covered by the absorbent article.

SUMMARY OF THE INVENTION

In one aspect, a disposable absorbent article for wearing about the lower torso of a wearer includes a first waist region, a second waist region, a crotch region disposed between the first and second waist regions, a first waist edge and a second waist edge, and a first longitudinal edge and a second longitudinal edge, the disposable absorbent article including a chassis that includes a topsheet, a backsheet, and an absorbent core disposed between the topsheet and the backsheet; the disposable absorbent article further including a leg gasketing system, wherein the leg gasketing system comprises a web of material forming an inner cuff and an outer cuff; wherein the inner cuff comprises an inner cuff folded edge and an inner cuff material edge and the outer cuff comprises an outer cuff folded edge and an outer cuff material edge, such that the web of material is folded laterally inward to form the outer cuff folded edge and folded laterally outward to form the inner cuff folded edge; wherein the disposable absorbent article comprises a first area located in the crotch region, a second area located in the second waist region, a third area located in the first waist region, a fourth area, and a fifth area, wherein the first area of the disposable absorbent article is more breathable than both the second area and the third area, and wherein the first area of the disposable absorbent article is less breathable than both the fourth area and the fifth area.

In another aspect, a disposable absorbent article for wearing about the lower torso of a wearer includes a first waist region, a second waist region, a crotch region disposed between the first and second waist regions, a first waist edge and a second waist edge, and a first longitudinal edge and a second longitudinal edge, the disposable absorbent article including a chassis that includes a topsheet, a backsheet, and an absorbent core disposed between the topsheet and the backsheet; the disposable absorbent article further including a leg gasketing system, wherein the leg gasketing system comprises a web of material forming an inner cuff and an outer cuff; wherein the inner cuff comprises an inner cuff folded edge and an inner cuff material edge and the outer cuff comprises an outer cuff folded edge and an outer cuff material edge, such that the web of material is folded laterally inward to form the outer cuff folded edge and folded laterally outward to form the inner cuff folded edge; wherein the disposable absorbent article comprises a first area located in the crotch region, a second area located in the second waist region, a third area located in the first waist region, a fourth area, and a fifth area, wherein the first area of the disposable absorbent article has an air permeability of about 15 to about 25 $m^3/m^2/min$, and the second and third areas of the disposable absorbent article have an air permeability of about 7 to about 15 $m^3/m^2/min$, and the fourth and fifth areas of the disposable absorbent article have an air permeability of about 25 to about 70 $m^3/m^2/min$.

In another aspect, a package includes at least ten disposable absorbent articles for wearing about the lower torso of a wearer, the disposable absorbent articles include a first waist region, a second waist region, a crotch region disposed between the first and second waist regions, a first waist edge and a second waist edge, and a first longitudinal edge and a second longitudinal edge, the disposable absorbent articles further including a chassis that includes a topsheet, a backsheet, and an absorbent core disposed between the topsheet and the backsheet; the disposable absorbent articles further including a leg gasketing system, wherein the leg gasketing system comprises a web of material forming an inner cuff and an outer cuff; wherein the inner cuff comprises an inner cuff folded edge and an inner cuff material edge and the outer cuff comprises an outer cuff folded edge and an outer cuff material edge, such that the web of material is folded laterally inward to form the outer cuff folded edge and folded laterally outward to form the inner cuff folded edge; wherein the disposable absorbent article comprises a first area located in the crotch region, a second area located in the second waist region, a third area located in the first waist region, a fourth area, and a fifth area, wherein a cross section of the first area of the disposable absorbent article contains less layers of material than both a cross section of the second area of the disposable absorbent article and a cross section of the third area of the disposable absorbent article.

The disposable absorbent articles described herein comprise leg gasketing systems that may comprise one web or multiple webs of material. The description and claims herein may refer to leg gasketing system embodiments that are formed from "a web of material." The recitation of "a web of material" encompasses a single continuous web of material, multiple webs of material that are joined together to become one web of material, or multiple distinct webs of material that are separate from the disposable absorbent article chassis, and form part of the leg gasketing system. The leg gasketing systems described herein may comprise N-fiber material or other non-woven materials.

BRIEF DESCRIPTION OF THE DRAWINGS

FIG. 2 is a schematic cross sectional view of the leg gasketing system of FIG. 1, taken along the lateral centerline. The leg gasketing system is shown in a flat, uncontracted state.

FIG. 3 is a schematic cross sectional view of the leg gasketing systems and chassis of FIG. 1, the cross section taken along the lateral centerline. The leg gasketing systems are shown in a flat, uncontracted state.

FIG. 10 is a schematic cross sectional view of an exemplary absorbent article as described herein.

DETAILED DESCRIPTION OF THE INVENTION

Figure 1:
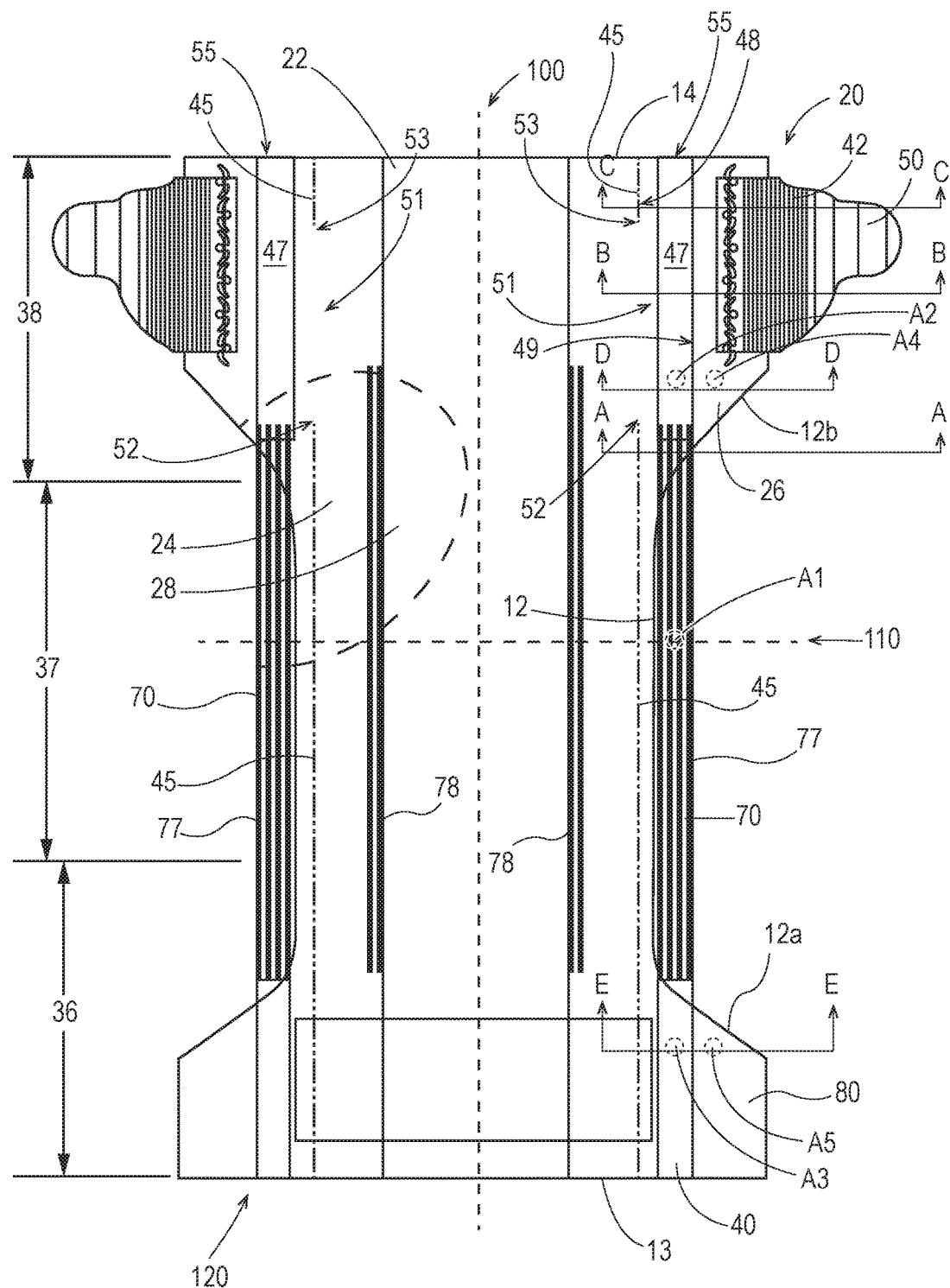
FIG. 1 is a schematic plan view of an absorbent article as detailed herein.

Definitions:

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Proximal" and "Distal" refer respectively to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal"

"Lateral" refers to a direction running from a longitudinal edge to an opposing longitudinal edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable."

"Extendibility" and "extensible" mean that the width or length of the component in a relaxed state can be extended or increased.

"Elasticated" and "elasticized" mean that a component comprises at least a portion made of elastic material.

"Elongatable material," "extensible material," or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Elastomeric material" is a material exhibiting elastic properties. Elastomeric materials may include elastomeric films, scrims, nonwovens, and other sheet-like structures.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

Absorbent Article:

The present disclosure is directed to a disposable absorbent article with a leg gasketing system that comprises a folded outer cuff having neatly finished outer cuff folded edges that creates an aesthetically pleasing design that is garment like, the absorbent article also including a leg gasketing system pocket with an opening towards the interior of the article, wherein the pocket reduces runny bowel movement leaks. The folded outer cuff design may be advantageous in preventing penetration and adhesive bleedthrough without the use of a polymeric film layer in the elasticized region. The absorbent article may comprise an opacity strengthening patch to provide the strength needed to prevent the article from extending excessively during application and wearing, and provide the opacity at the sides and waist to prevent the skin of the user from showing through the article.

FIG. 1 is a plan view of an absorbent article 20 of the present invention in a flat, uncontracted state. The garment-facing surface 120 of the absorbent article 20 is facing the viewer. The absorbent article 20 includes a longitudinal centerline 100 and a lateral centerline 110. The absorbent article 20 may comprise a chassis 22. The absorbent article 20 and chassis 22 are shown to have a first waist region 36, a second waist region 38 opposed to the first waist region 36, and a crotch region 37 located between the first waist region 36 and the second waist region 38. The waist regions 36 and 38 generally comprise those portions of the absorbent article 20 which, when worn, encircle the waist of the wearer. The waist regions 36 and 38 may include elastic elements such that they gather about the waist of the wearer to provide improved fit and containment. The crotch region 37 is the portion of the absorbent article 20 which, when the absorbent article 20 is worn, is generally positioned between the legs of the wearer.

The outer periphery of chassis 22 is defined by longitudinal edges 12 and waist edges (first waist edge 13 in first waist region 36 and second waist edge 14 in second waist region 38). The longitudinal edges 12 may be subdivided into a front longitudinal edge 12a, which is the portion of the longitudinal edge 12 in the first waist region 36, and a rear longitudinal edge 12b, which is the portion of the longitudinal edge 12 in the rear waist region 38. The chassis 22 may have opposing longitudinal edges 12 that are oriented generally parallel to the longitudinal centerline 100. However, for better fit, longitudinal edges 12 may be curved or angled to produce, for example, an "hourglass" shape diaper when viewed in a plan view. The chassis 22 may have opposing lateral edges 14 that are oriented generally parallel to the lateral centerline 110.

The chassis 22 may comprise a liquid permeable topsheet 24, a backsheet 26, and an absorbent core 28 between the topsheet 24 and the backsheet 26. In articles that include one or more opacity strengthening patches 80, the chassis 22 also comprises the opacity strengthening patch(es). The absorbent core 28 may have a body-facing surface and a garment facing-surface. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. The chassis 22 may comprise the main structure of the absorbent article 20 with other features added to form the composite absorbent article structure. While the topsheet 24, the backsheet 26, and the absorbent core 28 may be assembled in a variety of well-known configurations, preferred absorbent article configurations are described generally in U.S. Pat. Nos. 3,860,003; 5,151,092; 5,221,274; 5,554,145; 5,569,234; 5,580,411; and 6,004,306.

Topsheet:

The topsheet 24 is generally a portion of the absorbent article 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. One topsheet 24 useful herein is available from BBA Fiberweb, Brentwood, Tenn. as supplier code 055SLPV09U. The topsheet 24 may be apertured.

Any portion of the topsheet 24 may be coated with a lotion or skin care composition as is known in the art. Non-limiting examples of suitable lotions include those described in U.S. Pat. Nos. 5,607,760; 5,609,587; 5,635, 191; and 5,643,588. The specific examples are not limiting, as any lotion or skin care composition known in the art may be utilized. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

Absorbent Core:

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. At least a portion of the absorbent core may be substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but may be present in the absorbent core in an amount greater than about 80% by weight of the absorbent core, or greater than about 85% by weight of the absorbent core, or greater than about 90% by weight of the absorbent core, or greater than about 95% by weight of the core.

Exemplary absorbent structures for use as the absorbent core 28 are described in U.S. Pat. Nos. 4,610,678; 4,673, 402; 4,834,735; 4,888,231; 5,137,537; 5,147,345; 5,342, 338; 5,260,345; 5,387,207; 5,397,316; and 5,625,222.

Backsheet:

The backsheet 26 is generally positioned such that it may be at least a portion of the garment-facing surface 120 of the absorbent article 20. Backsheet 26 may be designed to prevent the exudates absorbed by and contained within the absorbent article 20 from soiling articles that may contact the absorbent article 20, such as bed sheets and undergarments. The backsheet 26 may be substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the absorbent article 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover and an inner layer. The outer cover may be made of a soft, non-woven material. The inner layer may be made of a substantially liquid-impermeable film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

Ears/Fasteners:

The absorbent article 20 may include front ears 40 and/or back ears 42. The ears 40, 42 may be extensible, inextensible, elastic, or inelastic. The ears 40, 42 may be formed from nonwoven webs, woven webs, knitted fabrics, polymeric and elastomeric films, apertured films, sponges, foams, scrims, and combinations and laminates thereof. The ears 40, 42 may be formed of a stretch laminate such as a nonwoven/elastomeric material laminate or a nonwoven/elastomeric material/nonwoven laminate. Stretch laminates may be formed by any method known in the art. For example, the ears 40, 42 may be formed as a zero strain stretch laminate, which includes at least a layer of non-woven material and an elastomeric element. The elastomeric element is attached to the layer of non-woven material while in a relaxed or substantially relaxed state, and the resulting laminate is made stretchable (or more stretchable over a further range) by subjecting the laminate to an activation process which elongates the nonwoven layer permanently, but the elastomeric element temporarily. The nonwoven layer may be integral with at least a portion of the chassis 22, in which case the elastomeric element may be attached to the nonwoven layer and the non-woven/elastomeric element laminate is subsequently activated. Alternatively, the nonwoven layer may be a separate component, in which case the elastomeric element is attached to the nonwoven layer to form the laminate, which is then coupled to the main portion. If one or more layers of the side panel are provided separately, the laminate may be activated either before or after attachment to the main portion. The zero strain activation processes is further disclosed in U.S. Pat. Nos. 5,167,897 and 5,156,793. A suitable elastic ear may be an activated laminate comprising an elastomeric film (such as is available from Tredegar Corp, Richmond, Va., as supplier code X25007) disposed between two nonwoven layers (such as is available from BBA Fiberweb, Brentwood, Tenn. as supplier code FPN332).

The ears 40, 42 may be discrete or integral. A discrete ear is formed as separate element which is joined to the chassis 22. An integral ear is a portion of the chassis 22 that projects laterally outward from the longitudinal edge 12. The integral ear may be formed by cutting the chassis form to include the shape of the ear projection.

The absorbent article 20 may also include a fastening system 50. When fastened, the fastening system 50 interconnects the first waist region 36 and the rear waist region 38 resulting in a waist circumference that may encircle the wearer during wear of the absorbent article 20. The fastening system 50 may comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963,140. The fastening system 50 may also include primary and secondary fastening systems, as disclosed in U.S. Pat. No. 4,699,622. The fastening system 50 may be constructed to reduce shifting of overlapped portions or to improve fit as disclosed in U.S. Pat. Nos. 5,242,436; 5,499,978; 5,507,736; and 5,591,152.

Figure 3A:
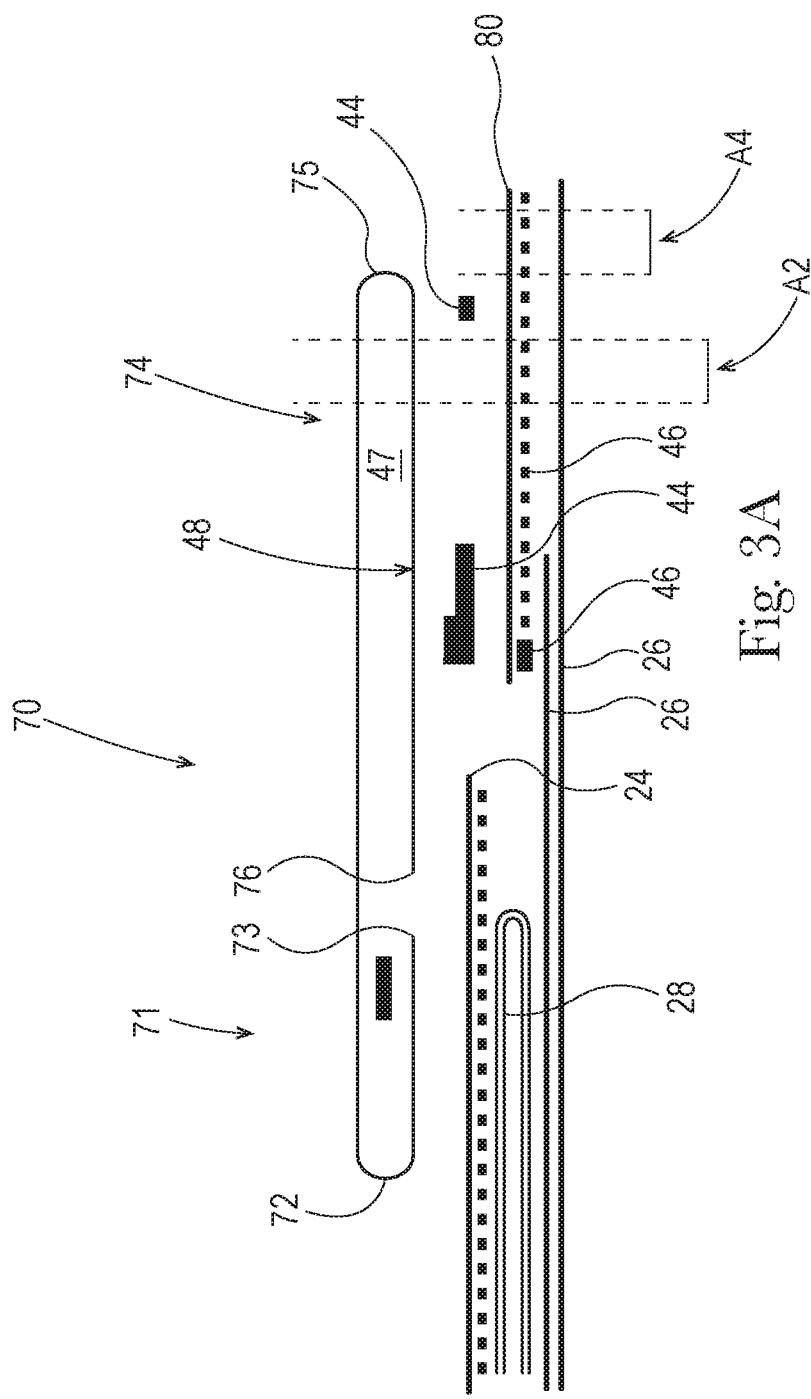
FIG. 3A is a schematic cross sectional view of the absorbent article of FIG. 1, the cross section taken along the line D-D.
Figure 3B:
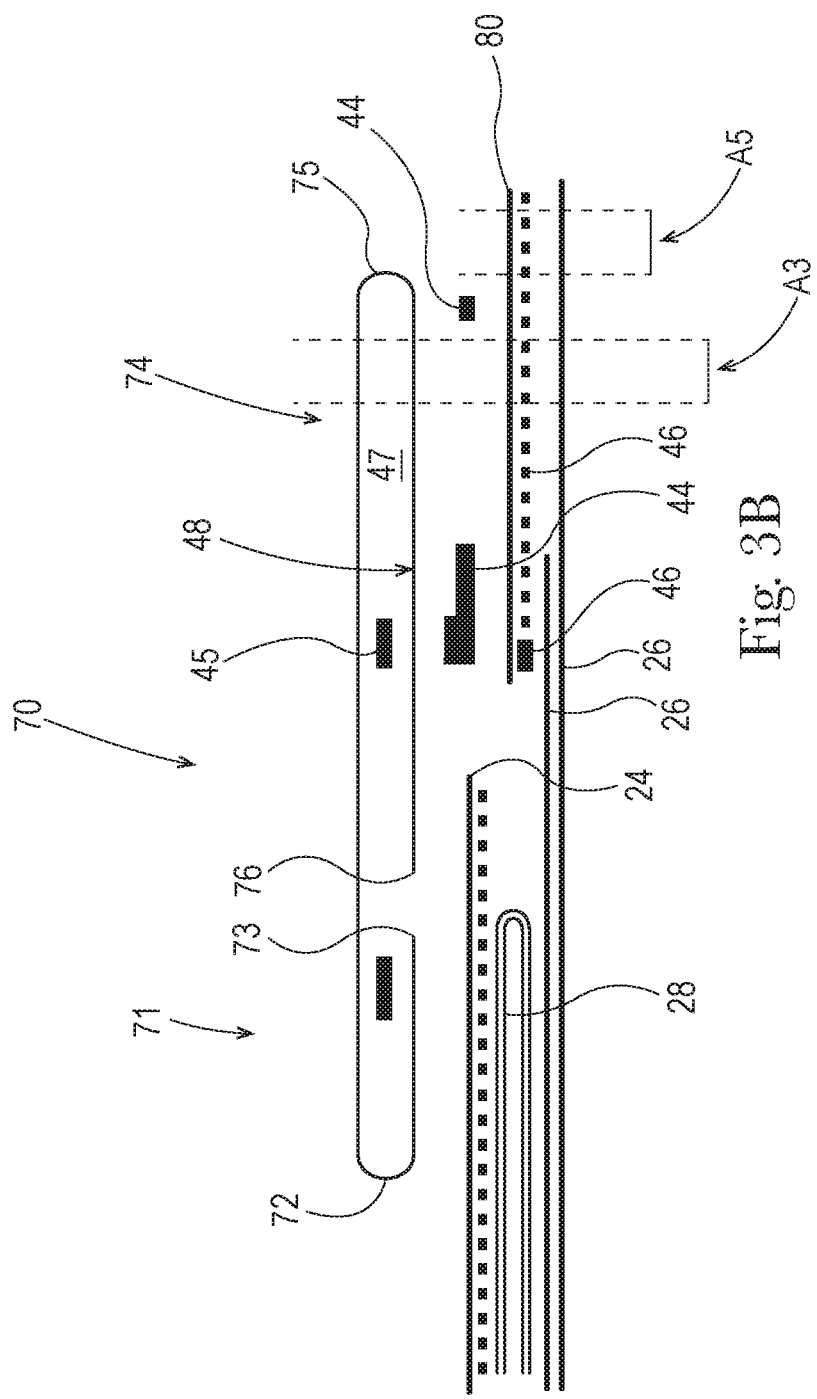
FIG. 3B is a schematic cross sectional view of the absorbent article of FIG. 1, the cross section taken along the line E-E.
Figure 4:
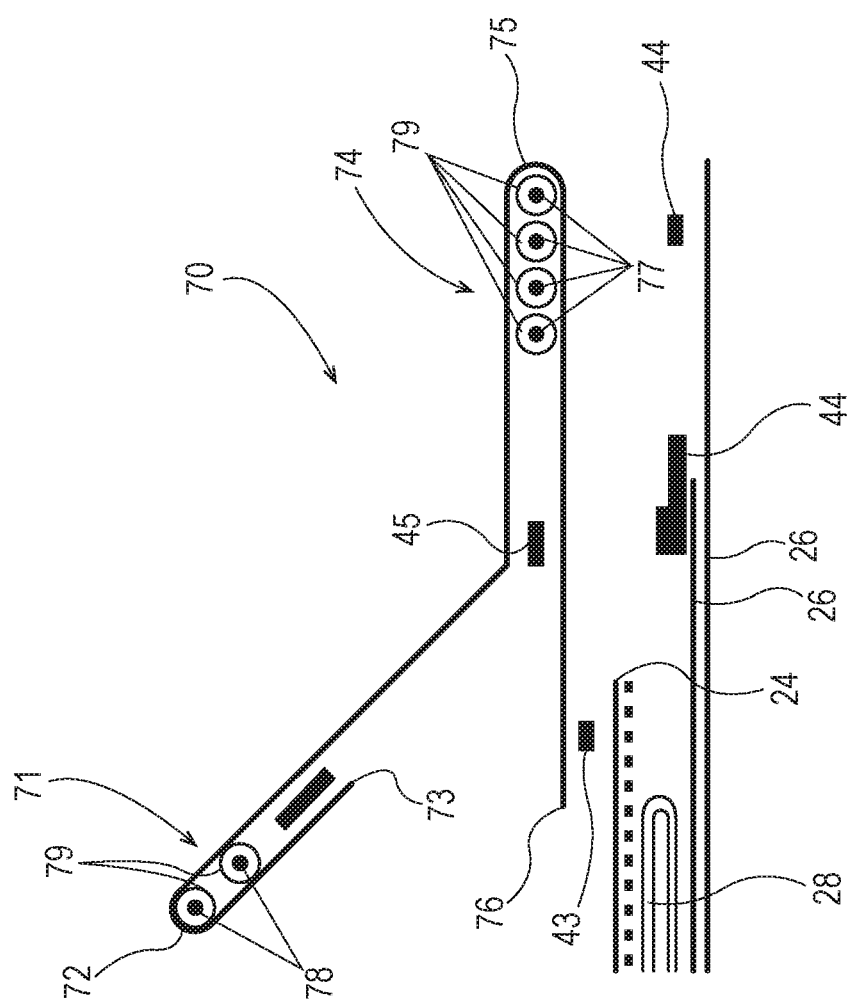
FIG. 4 is a schematic cross sectional view of the absorbent article of FIG. 1, the cross section taken along the line A-A.
Figure 5:
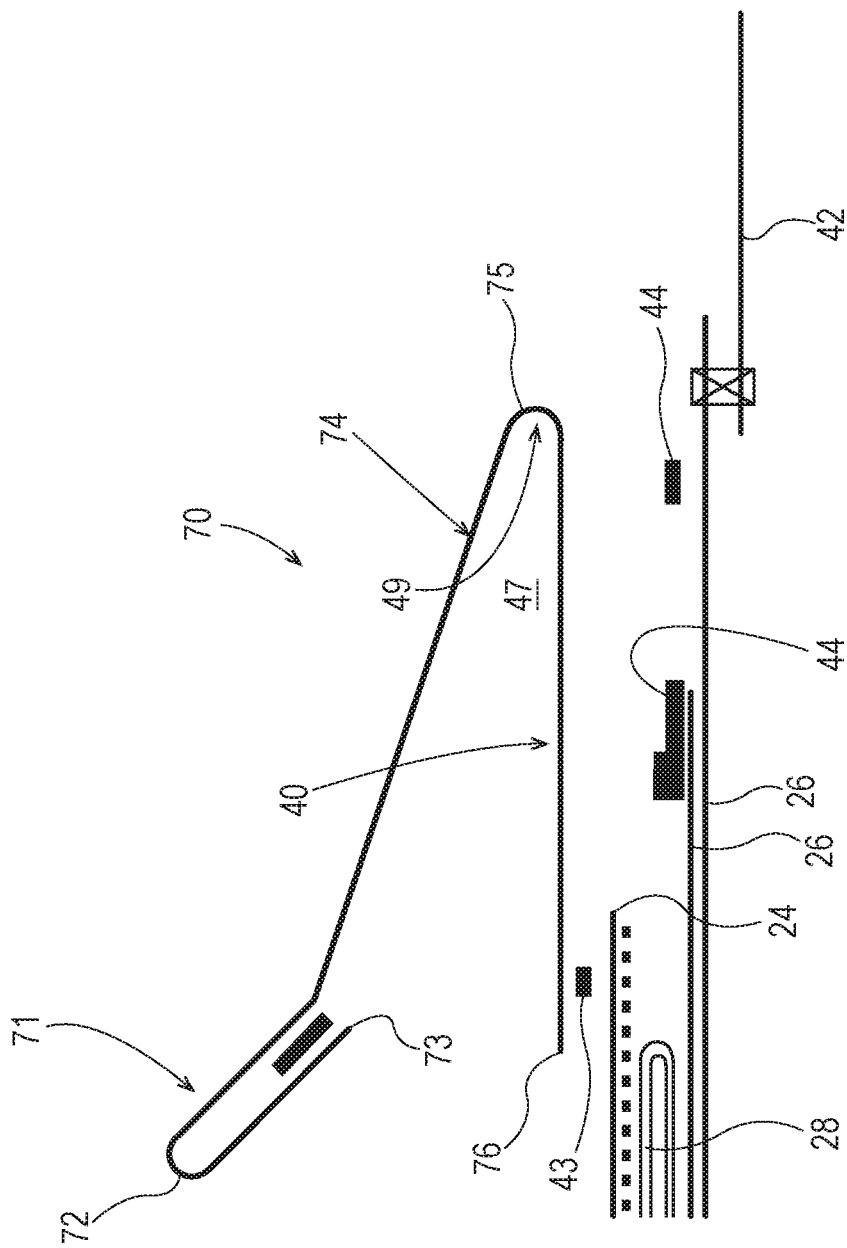
FIG. 5 is a schematic cross sectional view of the absorbent article of FIG. 1, the cross section taken along the line B-B.
Figure 6:
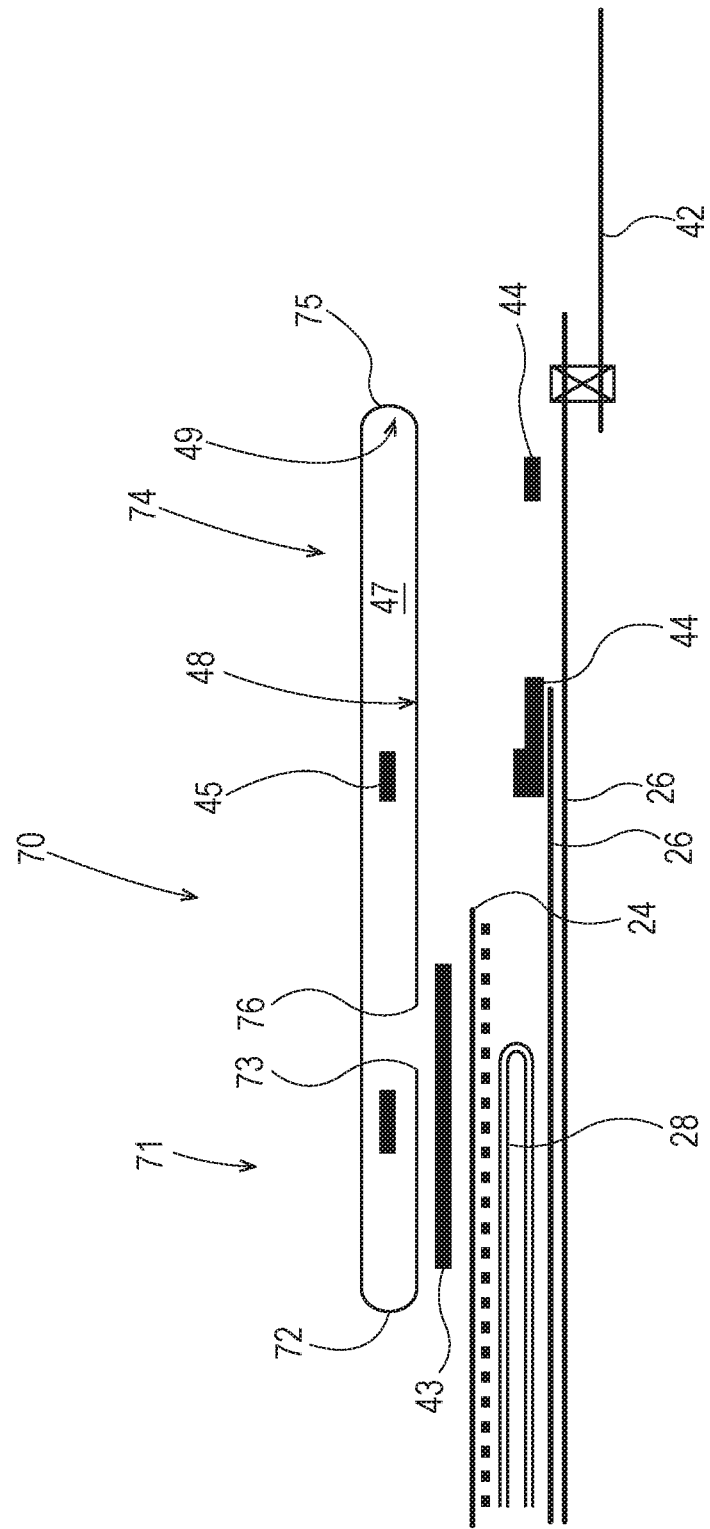
FIG. 6 is a schematic cross sectional view of the absorbent article of FIG. 1, the cross section taken along the line C-C.
Figure 7:
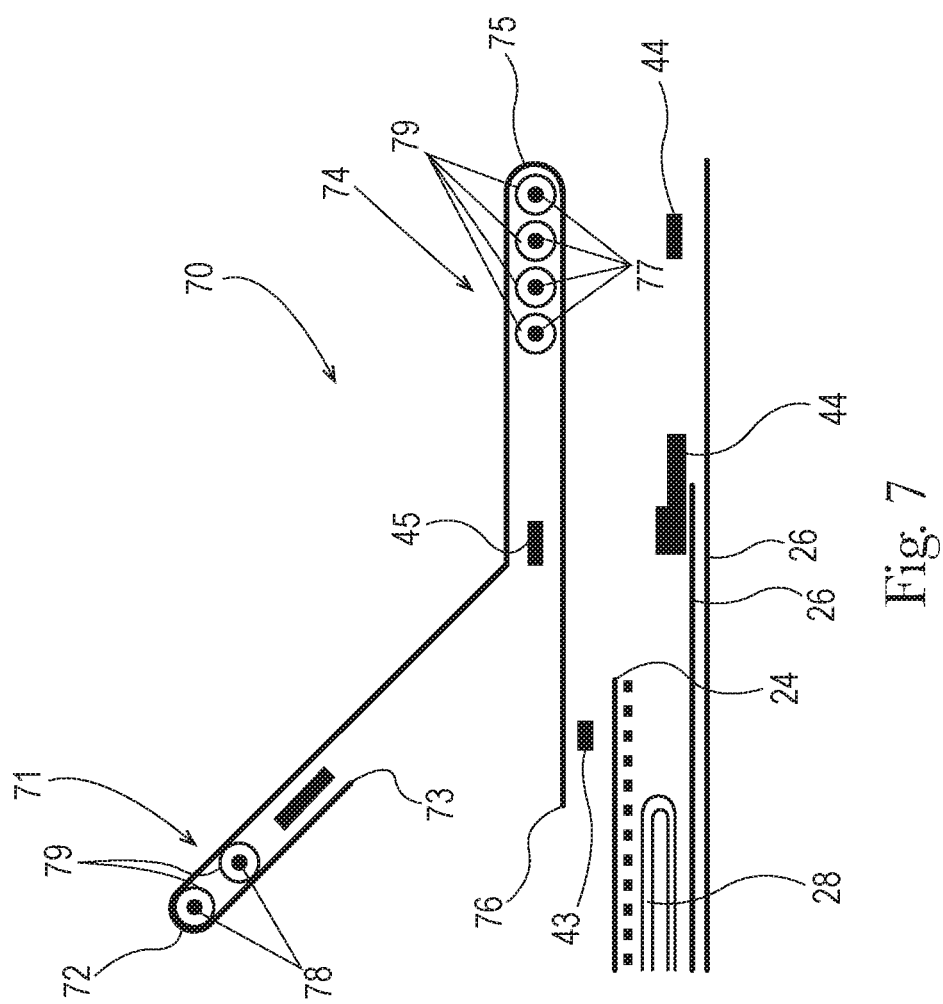
FIG. 7 is a schematic cross sectional view of the absorbent article of FIG. 1 with an opacity strengthening patch, the cross section taken along the line A-A.
Figure 8:
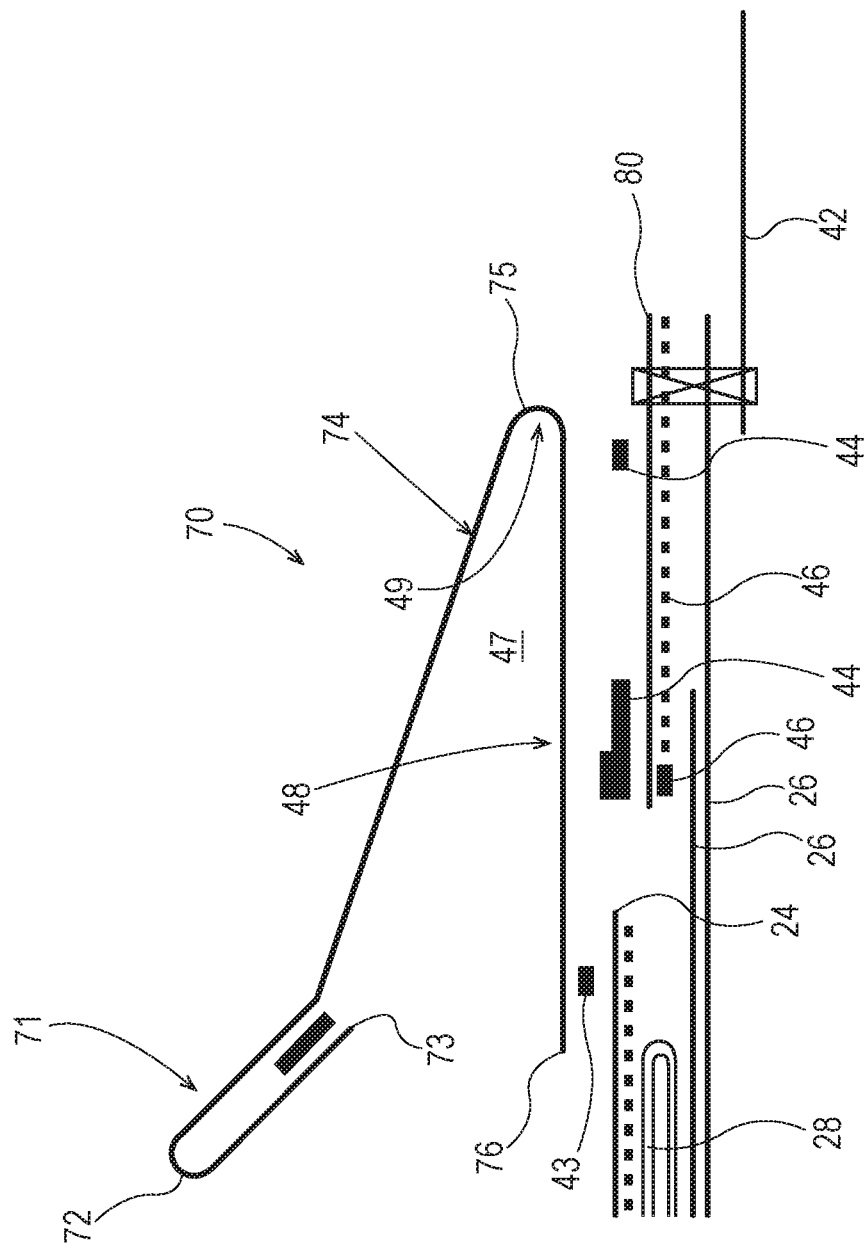
FIG. 8 is a schematic cross sectional view of the absorbent article of FIG. 1 with an opacity strengthening patch, the cross section taken along the line B-B.
Figure 9:
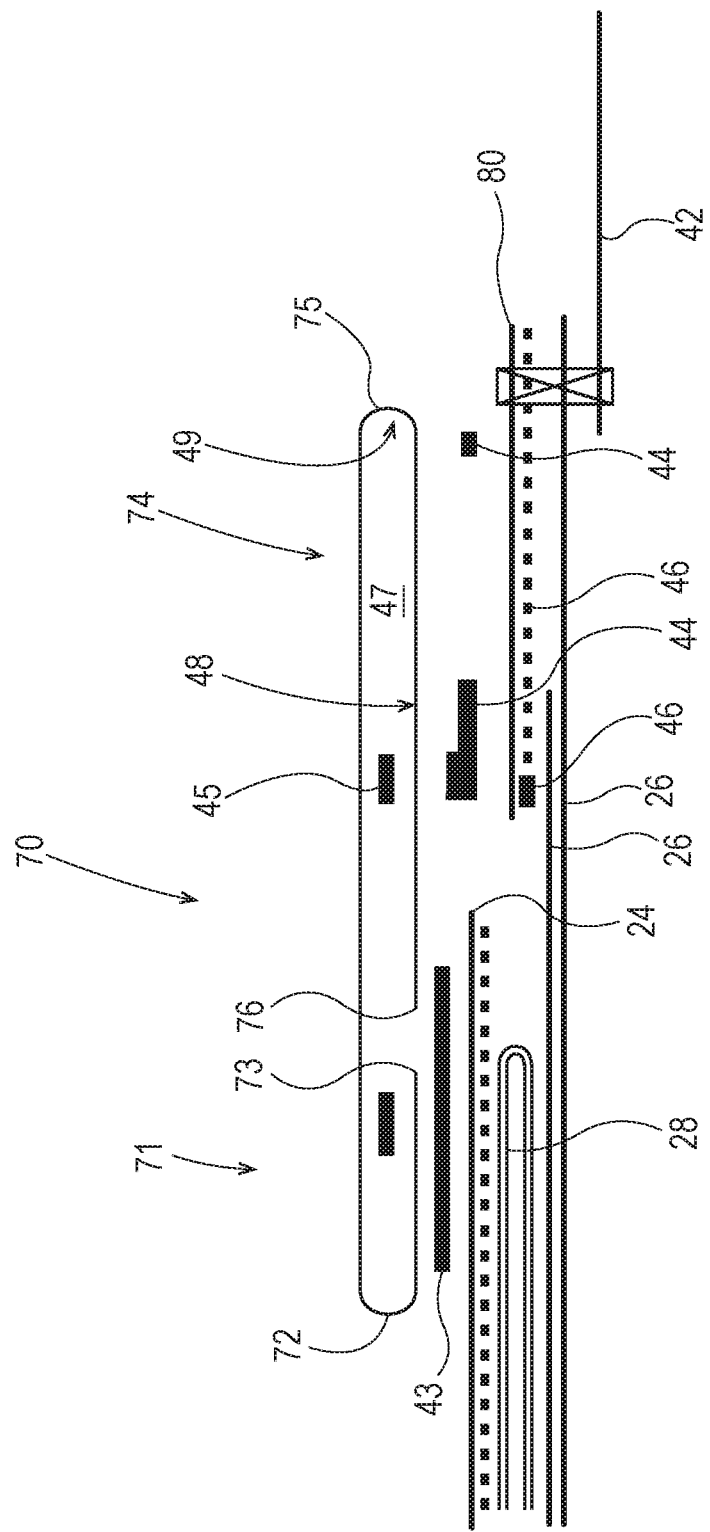
FIG. 9 is a schematic cross sectional view of the absorbent article of FIG. 1 with an opacity strengthening patch, the cross section taken along the line C-C.

Leg Gasketing System:

The absorbent article 20 may include a leg gasketing system 70 that is attached to the chassis 22. FIGS. 2 and 3 depict schematic cross sectional views of the exemplary leg gasketing system of FIG. 1 in a flat, uncontracted state, the views taken through the lateral centerline 110 (FIG. 2 is a schematic cross section of the left leg gasketing system, and FIG. 3 is a schematic cross section of both leg gasketing systems in relation to the topsheet). FIGS. 4-9 also depict schematic cross sectional views of the exemplary leg gasketing system 70 of FIG. 1. FIGS. 4-6 are cross sections of a version of the disposable absorbent article of FIG. 1 without an opacity strengthening patch 80, and FIGS. 7-9 are cross sections of a version of the disposable absorbent article of FIG. 1 with an opacity strengthening patch 80. In the article of FIGS. 7-9, the opacity strengthening patches 80 are located in the four corners of the diaper chassis 22, overlapping portions of both the polymeric film inner layer of the backsheet 26 and the ears 40, 42. FIGS. 4 and 7 are schematic cross sectional views through line A-A of FIG. 1. FIGS. 5 and 8 are schematic cross sectional views through line B-B of FIG. 1. FIGS. 6 and 9 are schematic cross sectional views through line C-C of FIG. 1. In the various articles, the leg gasketing system 70 may include an inner cuff 71 that has an inner cuff folded edge 72 and an inner cuff material edge 73. The leg gasketing system 70 may further include an outer cuff 74 that has an outer cuff folded edge 75 and an outer cuff material edge 76.

Each leg gasketing system 70 may comprise a single, continuous web of material. An leg gasketing system having a single web of material may provide a cost advantage over leg gasketing systems having more than one web of material. Further, a leg gasketing system formed from one web of material may have fewer leaks, as there are no holes created by bonding more than one web of material. Also, a leg gasketing system having one web of material may be more aesthetically pleasing, as few mechanical bonds are visible. The leg gasketing system 70 may be formed from more than one web of material (e.g., multiple webs of material that are joined together to become one web of material, or multiple distinct webs of material that are separate from the disposable absorbent article chassis and form part of the leg gasketing system). Herein, locations (e.g., folded edge, material edge, etc.) on the leg gasketing system 70 are detailed in reference to "a web of material" or "a portion of the web of material." The recitations of "a web of material" or "the web of material" refer to leg gasketing systems that may be formed from a single, continuous web of material, multiple webs of material that are joined together to become one web of material, or multiple distinct webs of material that are separate from the disposable absorbent article chassis and form part of the leg gasketing system. All such leg gasketing systems are contemplated.

The leg gasketing system 70 may include an inner cuff 71 that has an inner cuff folded edge 72 and an inner cuff material edge 73. The leg gasketing system 70 may further include an outer cuff 74 that has an outer cuff folded edge 75 and an outer cuff material edge 76. The web of material may be folded laterally inward (toward the longitudinal centerline 100 of the absorbent article 20) to form the outer cuff folded edge 75 and folded laterally outward (away from the longitudinal centerline 100 of the absorbent article 20) to form the inner cuff folded edge 72.

At least a portion of the web of material between the outer cuff folded edge 75 and the outer cuff material edge 76 may be attached to the chassis 22 (e.g., the topsheet 24, the backsheet 26, and/or the opacity strengthening patch 80) in the first waist region 36, the second waist region 38 and the crotch region 37. The attachment to the chassis 22 is made through utilization of one or more cuff attachment bonds 43, 44. One or more of the cuff attachment bonds 43, 44 may be continuous, or substantially continuous (e.g., in a continuously intermittent pattern) from the first waist edge 13 to the second waist edge 14. As seen in the exemplary article of FIGS. 3-6, a first cuff attachment bond 43 attaches at least a portion of the web of material between the outer cuff folded edge 75 and the outer cuff material edge 76 to the topsheet 24. And a second cuff attachment bond 44 attaches at least a portion of the web of material between the outer cuff folded edge 75 and the outer cuff material edge 76 to the inner layer of backsheet 26 (e.g., backsheet film). In FIGS. 3-6, a single first cuff attachment bond 43 and a single second cuff attachment bond 44 are shown, but articles having multiple first cuff attachment bonds 43 and/or multiple second cuff attachment bonds 44 are contemplated. As seen in FIGS. 7-9, a first cuff attachment bond 43 attaches at least a portion of the web of material between the outer cuff folded edge 75 and the outer cuff material edge 76 to the topsheet 24. And at least one second cuff attachment bond 44 attaches at least a portion of the web of material between the outer cuff folded edge 75 and the outer cuff material edge 76 to the opacity strengthening patch 80 in at least a portion of the first waist region 36 and at least a portion of the second waist region 38. The opacity strengthening patch is attached to the inner layer of backsheet 26 (e.g., backsheet film) by at least one OSP bond(s) 46. In the crotch region 37 and in a portion of the first waist region 36 and in a portion of the second waist region 38, at least a portion of the web of material between the outer cuff folded edge 75 and the outer cuff material edge 76 is attached to the backsheet 26 (inner or outer backsheet layer) through cuff attachment bond 44. In other words, from first waist edge 13 to second waist edge 14, at least a portion of the web of material between the outer cuff folded edge 75 and the outer cuff material edge 76 is attached to either the backsheet 26 or to the opacity strengthening patch 80 through continuous or substantially continuous second cuff attachment bond(s) 44. In FIGS. 7-9, a single first cuff attachment bond 43 is shown, but articles having multiple first cuff attachment bonds 43 are contemplated. The cuff attachment bonds 43, 44 and the OSP bonds 46 may take the form of glue, heat bond, pressure bond, CPW bonds, or any other bonding method known in the art. In FIGS. 3-9, the cuff attachment bonds 43, 44 and the OSP bonds 46 take the form of a glue bond.

Further, at least a portion of the web material between the inner cuff folded edge 72 and the outer cuff folded edge 75 is attached to at least a portion of the web of material between the outer cuff folded edge 75 and the outer cuff material edge 76 in at least the crotch region 37 and the first waist region 36. The attachment of the web of material between the inner cuff folded edge 72 and the outer cuff folded edge 75 to the web of material between the outer cuff folded edge 75 and the outer cuff material edge 76 in at least the crotch region 37 and the first waist region 36 is made through utilization of one or more cuff separation bonds 45. As seen in FIGS. 1-9, the cuff separation bond attaches at least a portion of the web material between the inner cuff folded edge 72 and the outer cuff folded edge 75 to the web of material between the outer cuff folded edge 75 and the outer cuff material edge 76 in the crotch region 37, the first waist region 36, and a portion of the second waist region 38. The cuff separation bond 45 may take the form of glue, heat bond, pressure bond, CPW bonds, or any other bonding method known in the art. In FIGS. 3-9, the cuff separation bond 45 takes the form of a glue bond.

As illustrated in FIGS. 1 and 4-9, the web of material between the inner cuff folded edge 72 and the outer cuff folded edge 75 is unattached to the web of material between the outer cuff folded edge 75 and the outer cuff material edge 76 in at least a portion of the second waist region 38. Due to the web of material between the inner cuff folded edge 72 and the outer cuff folded edge 75 being unattached to the web of material between the outer cuff folded edge 75 and the outer cuff material edge 76 in at least a portion of the second waist region 38, a leg gasketing system pocket 47 is formed in at least a portion of the second waist region of the leg gasketing system 70. The leg gasketing system pocket 47 includes an inboard longitudinal edge 48 and an outboard longitudinal edge 49, which define lateral dimensions of the leg gasketing system pocket. The inboard longitudinal edge 48 of the leg gasketing system pocket 47 may be coterminous with a line that the cuff separation bond 45 runs along in the longitudinal direction. The outboard longitudinal edge 49 may be coterminous with the outer cuff folded edge 75. Alternately, the outboard longitudinal edge 49 may be coterminous with the most outboard bond of the outer cuff 74.

The leg gasketing system pocket 47 may include an opening 51 which runs a distance along the inboard longitudinal edge 48 of the leg gasketing system pocket 47. The opening 51 is created by a break in the cuff separation bond 45. Referring to FIG. 1, the cuff separation bond 45 runs in the longitudinal direction of the absorbent article, and is continuous, or substantially continuous (e.g., in a continuously intermittent pattern) in the first waist region 36 and the crotch region 37. The continuous cuff separation bond 45 continues into the second waist region 38, but then stops for a defined distance and then starts again along the same longitudinal line. The distance in which the cuff separation bond 45 stops along that longitudinal line is the distance in which the web material between the inner cuff folded edge 72 and the outer cuff folded edge 75 is unattached to the web of material between the outer cuff folded edge 75 and the outer cuff material edge 76. Accordingly, this distance is the length of the opening 51 which runs along the inboard longitudinal edge 48 of the leg gasketing system pocket 47. The opening 51 has an inboard lateral edge 52 and an outboard lateral edge 53 where the cuff separation bond 45 starts and stops along the longitudinal line that the cuff separation bond 45 runs along. As illustrated in FIG. 1, the length of the opening 51 can be determined by measuring the distance between inboard lateral edge 52 and outboard lateral edge 53, taken along the longitudinal line that the cuff separation bond 45 runs along.

The leg gasketing system pocket 47 may include an opening 51 which again runs a distance along the inboard longitudinal edge 48 of the leg gasketing system pocket 47. The opening 51 is created by a series of breaks in the cuff separation bond 45. Referring to FIG. 1, the cuff separation bond 45 runs in the longitudinal direction of the absorbent article, and is continuous in the first waist region 36 and the crotch region 37. The continuous cuff separation bond 45 continues into the second waist region 38, but then becomes an intermittent bond pattern (e.g., stop-start-stop-start) for a defined distance and then becomes continuous again along the same longitudinal line. The distance in which the cuff separation bond 45 becomes an intermittent bond pattern along that longitudinal line is the distance in which the web material between the inner cuff folded edge 72 and the outer cuff folded edge 75 is intermittently attached to the web of material between the outer cuff folded edge 75 and the outer cuff material edge 76. This intermittent pattern for a distance of the cuff separation bond 45 creates series of small pockets, together referred to herein as a leg gasketing system pocket.

The pocket and opening can occur in the first waist region, the second waist region, or in the crotch region as needed for the specific type of exudates and the particular situation where leakage prevention is desired. For instance, a wearer who sleeps on their belly (front) may benefit from the pocket and opening being located in the front waist region, as to stop urine leakage out of the front waist during sleep. Likewise, it may be important to create the opening on the crotch region for users wearing the article in the standing position as to contain exudates that are likely to locate centrally in the article due to the force of gravity when in a standing position.

The opening 51 may measure between about 5 mm and about 100 mm in the longitudinal direction, or any range or distance within the range of about 5 mm to about 100 mm; in some articles the opening measures about 75 mm or about 50 mm; and in other articles the opening measures between about 1 mm and about 20 mm. The length of opening 51 may be between about 1% and about 75% of the overall longitudinal length of the leg gasketing system pocket 47 (or any range or percentage within the range of about 1% to about 75%). The overall longitudinal length of the leg gasketing system pocket 47 is the distance from the furthest longitudinally inboard portion of the pocket to the furthest longitudinally outboard portion of the pocket. As shown in FIG. 1, the overall longitudinal length of the leg gasketing system pocket 47 is the distance from the inboard lateral edge 52 of the opening 51 to the second waist edge 14 of the absorbent article 20, taken along the longitudinal line that the cuff separation bond 45 runs along. In other words, for the article shown in FIG. 1, the longitudinal dimensions of the leg gasketing system pocket 47 are defined by the inboard lateral edge 52 of the opening 51 and the second waist edge 14. The overall longitudinal length of the leg gasketing system pocket 47 may measure between about 5 mm and about 200 mm in the longitudinal direction, or any range or distance within the range of about 5 mm to about 200 mm; in some articles, about 100 mm, about 75 mm or about 50 mm; and alternately the overall longitudinal length measures between about 1 mm and about 20 mm.

The overall lateral width of the leg gasketing system pocket 47 is the distance from the furthest laterally inboard portion of the pocket to the furthest laterally outboard portion of the pocket. For the article shown in FIG. 1, the overall lateral width of the leg gasketing system pocket 47 is the distance from the inboard longitudinal edge 48 of the leg gasketing system pocket to the outboard longitudinal edge 49 of the leg gasketing system pocket, taken along a line that is parallel to the second waist edge 14 and centered in the middle of the opening 51 of the leg gasketing system pocket. In other words, for the exemplary article shown in FIG. 1, the lateral dimension of the leg gasketing system pocket 47 (i.e., the width) is defined by inboard and outboard longitudinal edges 48, 49 of the leg gasketing system pocket 47. The overall lateral width of the leg gasketing system pocket 47 may measure between about 5 mm and about 60 mm in the lateral direction, or any range or distance within the range of about 5 mm to about 60 mm; in some articles, about 30 mm, about 25 mm, or about 20 mm; and in other articles, the overall lateral width measures between about 1 mm and about 20 mm. The overall lateral width of the leg gasketing system pocket 47 may be between about 1% and about 75% of the overall longitudinal length of the leg gasketing system pocket 47 (or any range or percentage within the range of about 1% to about 75%). The length of opening 51 may be between about 20% and about 100% of the overall lateral width of the leg gasketing system pocket 47 (or any range or percentage within the range of about 20% to about 100%).

When a wearer of an absorbent article has a runny bowel movement, many times the runny bowel movement spreads upon defecation and leaks out of the absorbent article in an area between the leg cuffs and wearer's legs, or in an area between the waist region and the wearer's back. Leaks of this type often happen because the snug fit between user's body and the attached absorbent article do not allow enough room for the runny bowel movement to remain contained within the absorbent article during the wearer's movement. One advantage of the leg gasketing system pocket 47 as detailed herein, in combination with the leg gasketing system(s) as detailed herein, are the additional pocketed areas that provide extra void volumes within the leg cuffs for containment of bodily extrudate (e.g., fecal material). When the wearer moves, a portion of the bodily extrudate will migrate into the leg gasketing system pocket 47 for containment and be held/trapped between two layers of nonwoven within the leg gasketing system before it can leak out in an area between the wearer's back and the back waist region of the absorbent article or an area between the leg cuffs and wearer's legs of the absorbent article. Thus, the leg gasketing system pocket 47 detailed herein reduces leaks. Moreover, leg gasketing system pocket 47 provides additional void volume within the leg cuffs to receive the fecal material which helps in isolating the fecal material from wearer's skin and restricts flow towards the front by the separation sheet.

The leg gasketing system pocket 47 may be free of elastic members 77. The leg gasketing system pocket 47 may contain one or more snap back elastic members. The leg gasketing system pocket 47 may have a second opening 55 along the second waist edge 14 of the absorbent article. The leg gasketing system pocket 47 may be sealed along the second waist edge 14.

At least a portion of the web of material between the outer cuff folded edge 75 and the outer cuff material edge 76 may be attached to the chassis 22 (e.g., topsheet 24, backsheet 26, and/or opacity strengthening patch 80) in the first waist region 36, the second waist region 38 and the crotch region 37; and at least a portion of the web of material between the inner cuff folded edge 72 and the outer cuff folded edge 75 may be attached to the web of material between the outer cuff folded edge 75 and the outer cuff material edge 76 in the crotch region 37 and the first waist region 36; wherein the outer cuff includes an elastics adhesive 79 and at least one longitudinally oriented elastic member running parallel to the outer cuff folded edge 75, the elastics adhesive 79 and at least one elastic member disposed between 1) the web of material between the outer cuff folded edge 75 and the outer cuff material edge 76 and 2) the web of material between the outer cuff folded edge 75 and the inner cuff folded edge 72; wherein in at least a portion of the second waist region, the outer cuff is free of elastics adhesive 79 and elastic members 77, thus forming a leg gasketing system pocket 47 between 1) the web of material between the outer cuff folded edge 75 and the outer cuff material edge 76 and 2) the web of material between the outer cuff folded edge 75 and the inner cuff folded edge 72, the leg gasketing system pocket 47 having an outboard longitudinal edge 49 at the outer cuff folded edge 75; wherein the leg gasketing system pocket 47 comprises an opening 51 on an inboard longitudinal edge 48 of the leg gasketing system pocket.

The pocket 47 may include a thermal or compression bond that defines at least a portion of the perimeter of the pocket (e.g., the entire perimeter of the pocket), such that the at least a portion of the pocket 47 (e.g., the entire pocket), can be made visible to a wearer or caregiver as to signal the functionality of the pocket 47 prior to use.

The pocket 47 may extend to the lateral edge of the chassis and create channels for facilitating the flow of runny bowel movement. This open channel area can be sealed by any suitable bonding technique such as glue, mechanical bonds, thermal bonds, or the like.

The hydrophobic properties, such as Low Surface Tension Strikethrough or Hydro Head, can be increased in a least a portion of the pocket 47, in such a way that prevents exudates from leaking through the materials that comprise the pocket. Accordingly, this will maintain separation of the contained fecal material from the wearer. Increasing hydrophobic properties can be accomplished by applying hydrophobic coatings, inks, glues, silicones, additional materials, or any combination thereof, or by any other means known in the art.

The outer cuff 74 and inner cuff 71 may be the same color. The outer cuff 74 and inner cuff 71 may be different colors. There may be an additional printing on one or more of the cuffs of the leg gasketing system 70. In articles with printing on both the inner and outer cuffs, the printing may be the same or different on each cuff.

The leg gasketing system 70 may include a printed zone that outlines or defines at least a portion of the pocket 47 such that the benefit can be signaled prior to use.

The outer cuff 74 may comprise elastic members 77 positioned in a lateral array between the outer cuff folded edge 75 and outer cuff material edge 76. As illustrated in FIGS. 2-4, the elastics 77, 78 are attached to the portion of the web of material that forms the outer cuff by elastics adhesive 79. The elastics may be positioned between 1) the portion of the web of material between the outer cuff folded edge 75 and the outer cuff material edge 76, and 2) the portion of the web material between the outer cuff folded edge 75 and the inner cuff folded edge 72. The outer cuff 74 may comprise at least two elastic members 77, at least three elastic members 77, at least four elastic members 77, at least five elastic members 77, or at least six elastic members 77. The elastic members 77 may be disposed between the outer cuff folded edge 75 and the inner cuff material edge 73.

The inner cuff 71 may comprise an array of elastic members 78 positioned in a lateral array between the inner cuff folded edge 72 and the inner cuff material edge 73. The elastics attached to the portion of the web of material that forms the inner cuff by elastics adhesive 79. The elastics may be positioned between 1) the portion of the web of material between the inner cuff folded edge 72 and the inner cuff material edge 73, and 2) the portion of the web material between the inner cuff folded edge 72 and the outer cuff folded edge 75. The inner cuff 71 may comprise at least one elastic member 78, at least two elastic members 78, at least three elastic members 78, at least four elastic members 78, or at least five elastic members 78. The elastic members 78 may be disposed between the inner cuff folded edge 72 and the outer cuff material edge 76.

The outer cuff 74 may comprise at least one more elastic member 77 than the inner cuff 71 elastic member(s) 78. The inner cuff material edge 73 may be laterally outboard the outer cuff material edge 76.

The elastic members 77 and 78 may be spaced at least 2 mm apart from one edge of the member to the other edge of the member, optionally at least 3 mm apart; optionally at least 3.5 mm apart; optionally at least 4 mm apart; optionally at least 4.5 mm apart; optionally at least 5 mm apart; optionally at least 5.5 mm apart; optionally at least 6 mm apart; optionally at least 6.5 mm apart; optionally at least 7 mm apart; optionally at least 7.5 mm apart; optionally at least 8 mm apart; optionally at least 8.5 mm apart; optionally at least 9 mm apart; optionally at least 9.5 mm apart; optionally at least 10 mm apart; optionally at least 10.5 mm apart; optionally at least 11 mm apart; optionally at least 11.5 mm apart; optionally at least 12 mm apart. The outermost elastic members 77 and 78 may be less than about 2 mm from the outer cuff material edge 76 and inner cuff material edge 73; optionally less than about 1.5 mm, less than about 1 mm.

The outer cuff 74 may have four elastic members 77 that are about 4 mm apart. The outer cuff 74 may have four elastic members that are about 2 mm/7 mm/2 mm apart. The outer cuff 74 may have three elastic members 77 that are about 6 mm apart. The outer cuff 74 may have two elastic members that are about 12 mm apart. The outer cuff 74 may have two elastic members that are about 3 mm/6 mm/3 mm apart, as spaced from the outer cuff folded edge 75. The elastic members may be about 2 mm from the outer cuff folded edge 75, optionally about 0 mm from the outer cuff folded edge 75.

The leg gasketing system 70 may have an inner cuff 71 comprised of an inner cuff folded edge 72 and an inner cuff material edge 73. The leg gasketing system 70 may further comprise an outer cuff 74 comprising an outer cuff folded edge 75 and an outer cuff material edge 76. The leg gasketing system may comprise a first material comprising the inner cuff 71 and a second material comprising the outer cuff 74. The first and second material may overlap and be joined together along a longitudinal edge of each material by any suitable bonding means (i.e., a single web), or be separate webs of material. The web of material may be folded laterally inward to form the outer cuff folded edge 75 and folded laterally outward to form the inner cuff folded edge 72. The proximal edges of the outer cuff 74 may be coterminous. The proximal edges of the outer cuff 74 may be spaced greater than about 2 mm apart; greater than about 4 mm; greater than about 6 mm; greater than about 10 mm apart. The proximal material edges of the cuff may be both bonded to the inner cuff. Only one of the proximal material edges of the outer cuff 74 may be bonded to the inner cuff. The proximal material edges of the outer cuff are held together with any suitable bonding means.

The leg gasketing system 70 may be spaced laterally inward of the chassis longitudinal edge 12 by about 10 mm, optionally about 20 mm, optionally about 30 mm, optionally about 60 mm or more. The laterally outboard edge of the chassis may be defined by the lateral edge of the outer cuff. The backsheet and/or polymeric film may be spaced laterally inward of the outer cuff edge by about 10 mm; optionally about 20 mm; optionally about 30 mm; optionally about 40 mm.

The laterally outboard edge of the leg gasketing system 70 may be disposed laterally inboard of at least a portion of the longitudinal edge of the article in at least one of the waist regions. Thus, the front ears 40 and/or back ears 42 may extend past the leg gasketing system 70.

The height of the inner cuff 71 may be at least about 10 mm, at least about 20 mm, a least about 30 mm, at least about 32 mm, at least about 35 mm, at least about 38 mm. The height of the outer cuff 74 may be at least about 15 mm, at least about 23 mm, at least about 25 mm, at least about 27 mm, at least about 30 mm. The height of the inner cuff is measured from inner cuff folded edge 72 to the first point of connection to a material beyond the inner cuff material edge 73 in the crotch region. The outer cuff height is measured from the outer cuff folded edge 75 to the first point of connection the inner cuff 72 has to a material beyond the inner cuff material edge 73 in the crotch region. Thus, the inner and outer cuffs are measured from their respective folded edges to the point where the inner cuff is connected to the first material beyond the inner cuff material edge.

One advantage of the leg gasketing system 70 detailed herein is that when a substantially liquid-impervious material is used in construction of the cuff, the polymeric film layer may be narrowed or not present at all, resulting in more cost effective designs. Utilizing adhesive technologies that are more reliably processed results in more reliable performance and creates substantially liquid impervious seals. This technology enables narrowing the film layer to be only slightly wider than the absorbent core by reducing the need for redundant seals.

The backsheet polymeric film may be less than about 50 mm wider than the absorbent core; optionally less than about 40 mm wider, less than about 30 mm wider. The backsheet polymeric film may be at least about 20 mm more narrow than the chassis width; optionally at least about 40 mm more narrow than the chassis width; optionally at least about 60 mm more narrow than the chassis width; optionally at least about 80 mm more narrow than the chassis width; optionally at least about 100 mm more narrow than the chassis width; optionally at least about 120 mm more narrow than the chassis width.

The leg cuff may be joined to the topsheet and/or backsheet by a slot coated adhesive. At least about 12 gsm of adhesive may be applied; optionally at least about 15 gsm of adhesive is applied; optionally at least about 20 gsm of adhesive is applied; optionally, at least about 25 gsm of adhesive is applied; optionally at least about 40 gsm of adhesive is applied; optionally at least about 60 gsm of adhesive is applied. The adhesive may be at least about 1 mm wide; optionally at least about 3 mm wide; optionally at least about 7 mm wide. The adhesive may be at least about 2 mm inboard of the outboard lateral edge of the film; optionally at least 4 mm inboard of the outboard lateral edge of the film; optionally at least about 6 mm inboard of the outboard lateral edge of the film. The leg cuff may be joined to the topsheet and/or backsheet by two overlapping and redundant spiral adhesive sprays; optionally three overlapping and redundant spiral adhesive sprays.

The descriptions of the invention including the pocket 47 and opening 51 that allow for trapping exudates can be used in conjunction with an article that does not contain an absorbent core. This is useful for a product that is designed to be used in the medical industry as it can enable the collection of exudates for analysis easier without the exudates being absorbed into the product.

Figure 11Q:
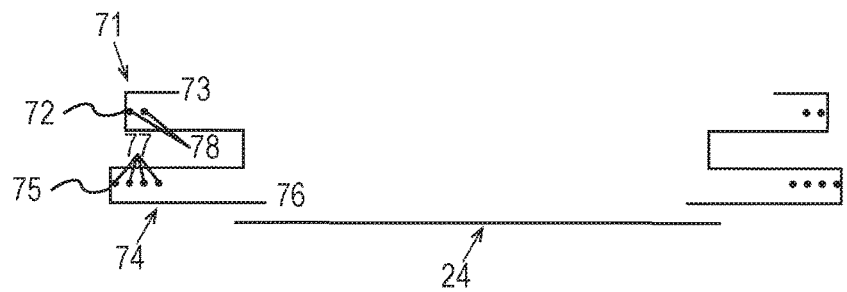
FIGS. 11A-T are schematic cross sectional views of additional exemplary leg gasketing systems suitable for use in the absorbent articles detailed herein.
Figure 11R:
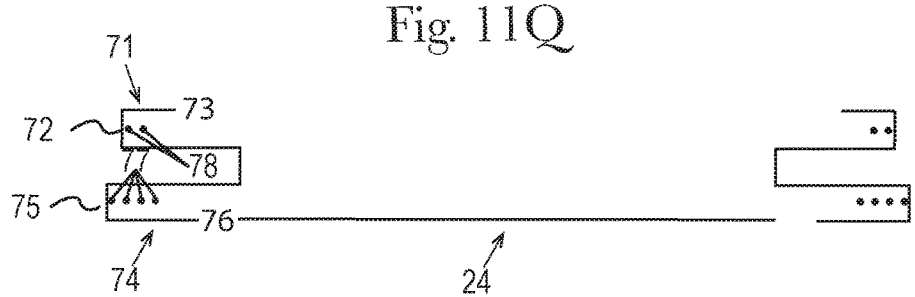
Figure 11S:
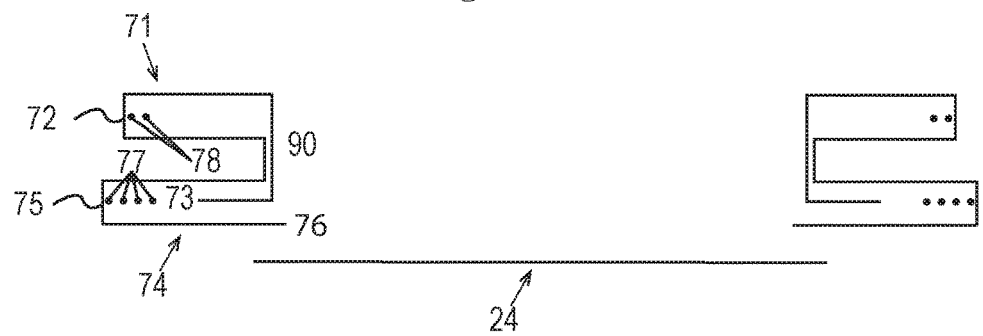
Figure 11T:
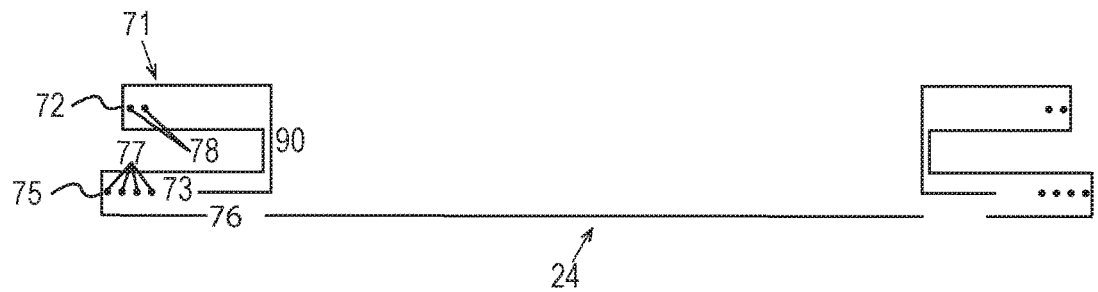

Additional exemplary leg gasketing systems 70 that may be useful in the absorbent articles detailed herein are shown in FIGS. 11*a*-11*t* of the accompanying drawings.

Opacity Strengthening Patch:

An opacity strengthening patch 80 may be included as part of the chassis 22. The opacity strengthening patch 80 is an additional layer of material. The opacity strengthening patch 80 may be connected to the leg gasketing system 70, the polymeric film layer, or the backsheet 26. The opacity strengthening patch 80 may be disposed between the backsheet 26 and leg gasketing system 70 in either the first waist region 36, the second waist region 38, or both the first waist region 36 and the second waist region 38 of the article; the opacity strengthening patch 80 may overlap at least one of the leg gasketing system 70 and/or the polymeric film layer (i.e., inner layer of the backsheet 26). The opacity strengthening patch 80 may be attached to one or both of the leg gasketing system 70 or the polymer film layer using any suitable means such as glue, mechanical bonds, thermal bonds, or the like, so that loads generated during the application process or during wear can be transferred from the lateral edge of the article to the leg gasketing system 70 and/or the polymeric film layer. The opacity strengthening patch is useful in providing the strength needed to prevent the article from extending excessively during application and wearing; it also may provide opacity at the sides and waist to prevent the skin of the user from showing through the article. Thus, the patch 80 may be located at any portion of the chassis 22 where strength and opacity is desirable. Materials suitable to act as the opacity strengthening patch include materials having a basis weight of at least about 10 gsm, at least about 15 gsm, at least about 25 gsm. An opacity strengthening patch useful herein may exhibit the following tensile properties in the cross direction: at 2% engineering strain for a 1 inch wide sample, 0.4N; at 5% engineering strain for a 1 inch wide sample, 1.25N; at 10% engineering strain for a 1 inch wide sample, 2.5N. One opacity strengthening patch useful herein is available from Pegas, Znojmo, CZ, as supplier number 803968.

The opacity strengthening patch 80 may be discrete and is located in the front and back waist regions of the article. The opacity strengthening patch may be about 70 mm long in the front, optionally about 90 mm long in the front; optionally about 120 mm long in the front. The opacity strengthening patch may be about 70 mm long in the back, optionally about 100 mm long in the back, optionally about 140 mm long in the back. The opacity strengthening patch may be continuous and spans the entire length of the product.

The opacity strengthening patch may have a hunter color opacity of greater than about 15%, optionally greater than about 25%, optionally greater than about 40%, optionally greater than 60%.

The opacity strengthening patch may be laterally outboard of the polymeric film layer. The opacity strengthening patch may overlap the polymeric film layer in the lateral direction such that it can be affixed to the polymeric film in order to transmit laterally directed application and wearing forces from the opacity strengthening patch to the polymeric film layer. Any suitable bonding means known in the art may be used to affix the opacity strengthening patch to the polymeric film layer. The opacity strengthening patch may overlap the polymeric film layer by about 5 mm, optionally about 10 mm, optionally about 15 mm, optionally about 20 mm, optionally less than about 30 mm.

There may be a lateral gap between the opacity strengthening patch and the polymeric film layer and the opacity strengthening patch is affixed by any suitable bonding means to the leg gasketing system, and the leg gasketing system is affixed to the polymeric film layer by any suitable bonding means such that application and wearing loads can transmit from the opacity strengthening patch to the gasketing system and then from the gasketing system to the polymeric film layer. The gap may preferably be less than 30 mm, more preferably less than 20 mm, more preferably less than 10 mm.

There may be a lateral gap between the opacity strengthening patch and the polymeric film layer; the opacity strengthening patch may be affixed by any suitable bonding means to the leg gasketing system and the body facing and garment facing sides of the leg gasketing system may be affixed together by any suitable bonding means so that the loads from the opacity strengthening patch are shared by both layers of the leg gasketing system. The leg gasketing system may be affixed to the polymeric film layer by any suitable bonding means such that application and wearing loads can transmit from the opacity strengthening patch to the leg gasketing system and then from the leg gasketing system to the polymeric film layer.

The opacity strengthening patch may overlap the leg gasketing system in the lateral direction such that it can be affixed securely to the opacity strengthening patch layer by any suitable bonding means as a way to transmit application and wearing forces from the opacity strengthening patch to the leg gasketing system. The opacity strengthening patch may overlap the leg gasketing system by about 5 mm, optionally about 10 mm, optionally less than about 15 mm, optionally less than about 25 mm.

The leg gasketing system may have about the same lateral tensile strength properties as the opacity strengthening patch. The combined properties of the leg gasketing system and the backsheet nonwoven outer cover may have about the same lateral tensile strength as the opacity strengthening patch. Alternately, the outercover nonwoven may have very low lateral strength between about 0% and about 10% engineering strain. The outercover nonwoven may exhibit the following tensile properties: at 10% engineering strain for a 1 inch wide sample, 0.4N.

Construction Materials:

It is recognized that there are many combinations of material lateral tensile properties that could form a substantially suitable force transmission pathway in the waist region or the article without excessive lateral stretch in the waist region, and that the material force pathways may go from the opacity strengthening patch directly into the polymeric film layer or into the polymeric film layer through a variety of other layers in the region immediately outboard the polymeric film layer. These layers may include the topsheet, backsheet nonwoven, cuff, absorbent assembly, leg gasketing system, or any other layer that is located in a region adjacent to the polymeric film layer.

The material of the leg gasketing system 70 may be made from a substantially liquid impervious material. The material may be selected from the group consisting of an SMS nonwoven, SMMS nonwoven material, or a nonwoven component layer comprising "N-fibers".

Various nonwoven fabric webs may comprise spunbond, meltblown, spunbond ("SMS") webs comprising outer layers of spunbond thermoplastics (e.g., polyolefins) and an interior layer of meltblown thermoplastics. The leg gasketing cuff 70 may comprise a nonwoven component layer having fine fibers ("N-fibers") with an average diameter of less than 1 micron (an "N-fiber layer") may be added to, or otherwise incorporated with, other nonwoven component layers to form a nonwoven web of material. The N-fiber layer may be used to produce a SNS nonwoven web or SMNS nonwoven web, for example.

The leg gasketing cuff 70 may comprise a first nonwoven component layer comprising fibers having an average diameter in the range of about 8 microns to about 30 microns, a second nonwoven component layer comprising fibers having a number-average diameter of less than about 1 micron, a mass-average diameter of less than about 1.5 microns, and a ratio of the mass-average diameter to the number-average diameter less than about 2, and a third nonwoven component layer comprising fibers having an average diameter in the range of about 8 microns to about 30 microns. The second nonwoven component layer is disposed intermediate the first nonwoven component layer and the third nonwoven component layer.

The N-fibers may be comprised of a polymer, e.g., selected from polyesters, including PET and PBT, polylactic acid (PLA), alkyds, polyolefins, including polypropylene (PP), polyethylene (PE), and polybutylene (PB), olefinic copolymers from ethylene and propylene, elastomeric polymers including thermoplastic polyurethanes (TPU) and styrenic block-copolymers (linear and radial di- and tri-block copolymers such as various types of Kraton), polystyrenes, polyamides, PHA (polyhydroxyalkanoates) and e.g. PHB (polyhydroxubutyrate), and starch-based compositions including thermoplastic starch, for example. The above polymers may be used as homopolymers, copolymers, e.g., copolymers of ethylene and propylene, blends, and alloys thereof. The N-fiber layer may be bonded to the other nonwoven component layers by any suitable bonding technique, such as the calender bond process, for example, also called thermal point bonding.

The use of an N-fiber layer in a nonwoven web may provide a low surface tension barrier that is as high as other nonwoven webs that have been treated with a hydrophobic coating or a hydrophobic melt-additive, and still maintain a low basis weight (e.g., less than 15 gsm or, alternatively, less than 13 gsm). The use of the N-fiber layer may also provide a soft and breathable (i.e., air permeable) nonwoven material that may be used in single web layer configurations in applications which previously used double web layer configurations. Furthermore, the use of the N-fiber layer may at least reduce the undesirable migration of hydrophilic surfactants toward the web and, therefore, may ultimately result in better leak protection for an associated absorbent article. Also, when compared to an SMS web having a similar basis weight, the use of a nonwoven web comprising the N-fiber layer may decrease the number of defects (i.e., holes or pinholes through the mechanical bond site) created during the mechanical bonding process. N-fibers are further discussed in WO 2005/095700 and U.S. patent application Ser. No. 13/024,844.

The inner cuff 71 web of material may have a hydrostatic head of greater than about 2 mbar, greater than about 3 mbar, greater than about 4 mbar. The outer cuff 74 web of material may have a hydrostatic head of less than about 200 mbar, less than about 100 mbar, less than about 75 mbar, less than about 50 mbar, less than about 25 mbar, less than about 15 mbar.

The folded outer cuff web of material may have a basis weight of 10 gsm; optionally 13 gsm; optionally 15 gsm; optionally 18 gsm.

The inner cuff 71 web of material may have an opacity of from about 15% to about 50% hunter opacity; optionally from about 20% to about 45% hunter opacity. The outer cuff 74 web of material may have an opacity of from about 45% to about 75% hunter opacity; optionally from about 50% to about 70% hunter opacity; optionally less than about 75% hunter opacity; optionally less than about 70% hunter opacity.

The inner cuff 71 web of material may have an air permeability of less than about 50 $m^3/m^2/min$; optionally less than about 45 $m^3/m^2/min$. The outer cuff 74 web of material may have an air permeability of greater than about 5 $m^3/m^2/min$; optionally greater than about 10 $m^3/m^2/min$; optionally greater than about 15 $m^3/m^2/min$; optionally greater than about 20 $m^3/m^2/min$.

The inner cuff 71 web of material may have a WVTR of less than about 5500 $g/m^2/24$ hrs; optionally less than about 5400 $g/m^2/24$ hrs. The outer cuff 74 web of material may have a WVTR of greater than about 4250 $g/m^2/24$ hrs; optionally greater than about 4500 $g/m^2/24$ hrs; optionally greater than about 5000 $g/m^2/24$ hrs; optionally greater than about 5250 $g/m^2/24$ hrs; optionally greater than about 5500 $g/m^2/24$ hrs.

The gasketing cuffs 70 may be substantially inelastic or may be elastically extensible to dynamically fit at the wearer's leg. The gasketing cuff 70 may be formed by one or more elastic members 77 and 78 (such as elastic strands) operatively joined to the topsheet 24, backsheet 26, or any other suitable substrate used in the formation of the absorbent article 20. Suitable gasketing cuff construction is further described in U.S. Pat. No. 3,860,003

The inner cuff 71 may span the entire longitudinal length of the absorbent article 20. The inner cuff 71 may be formed by a flap and an elastic member 78 (such as elastic strands). The inner cuff 71 may be a continuous extension of any of the existing materials or elements that form the absorbent article 20.

The inner cuff 71 may comprise a variety of substrates such as plastic films and woven or nonwoven webs of natural fibers (e.g., wood or cotton fibers), synthetic fibers (e.g., polyester or polypropylene fibers), or a combination of natural and synthetic fibers. The flap may comprise a nonwoven web such as spunbond webs, meltblown webs, carded webs, and combinations thereof (e.g., spunbond-meltblown composites and variants). Laminates of the aforementioned substrates may also be used to form the flap. A particularly suitable flap may comprise a nonwoven available from BBA Fiberweb, Brentwood, Tenn. as supplier code 30926. A particularly suitable elastic member is available from Invista, Wichita, Kans. as supplier code T262P. Further description of diapers having inner barrier cuffs and suitable construction of such barrier cuffs may be found in U.S. Pat. Nos. 4,808,178 and 4,909,803. The elastic member 78 may span the longitudinal length of the inner cuff 71. The elastic member 78 may span at least the longitudinal length of the inner cuff 71 within the crotch region 37. It is desirable that the elastic member 78 exhibits sufficient elasticity such that the inner cuff 71 remains in contact with the wearer during normal wear, thereby enhancing the barrier properties of the inner cuff 71. The elastic member 78 may be connected to the flap at opposing longitudinal ends. The flap may be folded over onto itself so as to encircle the elastic member 78.

The inner cuff 71 and/or outer cuff 74 may be treated, in full or in part, with a lotion, as described above with regard to topsheets, or may be fully or partially coated with a hydrophobic surface coating as detailed in U.S. application Ser. No. 11/055,743, which was filed Feb. 10, 2005. Hydrophobic surface coatings usefully herein may include a non-aqueous, solventless, multicomponent silicone composition. The silicone composition includes at least one silicone polymer and is substantially free of aminosilicones. A particularly suitable hydrophobic surface coating is available from Dow Corning MI, Salzburg as supplier code 0010024820.

The absorbent articles detailed herein may comprise a first area A1, a second area A2, a third area A3, a fourth area A4, and a fifth area A5. The first area A1 through fifth area A5 are illustrated in FIGS. 1-3B, shown on the right side of the absorbent article. In absorbent articles that are symmetrical along the longitudinal axis, the article will have a corresponding first area through fifth area on the left side of the absorbent article as well. The absorbent articles described herein are symmetrical along the longitudinal axis 100, and therefore will have two first areas (a left and a right), two second areas (a left and a right), two third areas (a left and a right), two fourth areas (a left and a right), and two fifth areas (a left and a right). The left areas, although not illustrated specifically, will be in the mirrored locations on the left side of the article as the illustrated right areas A1-A5. The first area A1 is located on the outer cuff 74 in the crotch region 37, specifically along the lateral centerline 110, and is breathable. The location of the first area A1 is also laterally inboard of the outer cuff folded edge 75 of the leg gasketing system. For example, in the absorbent article shown in FIGS. 1-3, the location of first area A1 may also be centered on a line that runs in the longitudinal direction and is parallel to the longitudinal centerline 100, wherein the line evenly splits the middle two longitudinally running elastics of the outer cuff. Accordingly, the intersection of this longitudinally running line and the lateral centerline 110 is the center of the location of the first area A1. In products that don't have four elastics like the illustrated embodiments, the longitudinally running line for centering the first area A1 may be a line parallel to the longitudinal centerline 100 that is inboard of the outer cuff folded edge by 5 mm.

At least one of the second area A2, located in the second waist region 38 on the outer cuff 74 of the leg gasketing system, and third area A3, located in the first waist region 36 on the outer cuff 74 of the leg gasketing system, are also breathable. The second area A2 and the third area A3 are longitudinally outboard of the first area A1. The second area A2 and the third area A3 and the first area A1 are laterally equidistant from the longitudinal centerline 100 of the absorbent article. Accordingly, the longitudinally running line for centering the first area A1 also runs through the center of the second area A2 and the third area A3. The first area A1, second area A2 and third area A3 may all be breathable. The first area A1 may be breathable to enable transpiration of water vapor from the crotch region of the absorbent article where urine may be most concentrated, reducing the interior humidity for skin health and comfort. The second area A2 and the third area A3 may be breathable to enable sweat from the hip region of the wearer to evaporate, reducing the likelihood of anhidrosis in this region. The first area A1 may be more breathable than the second area A2 and/or the third area A3 since the first area A1 is closer to the urine loading point in the article. The WVTR of the first area A1 may be at least about 4000 g/m²/24 hr and the WVTR of the second area A2 and the third area A3 may be at least about 3800 g/m²/24 hr. The WVTR of the first area A1 may be in the range of about 4000 to about 6000 g/m²/24 hr (or 4200 to 5000 g/m²/24 hr) and the WVTR of the second area A2 and the third area A3 may be in the range of about 3800 to about 5500 g/m²/24 hr (or 4000 to 5200 g/m²/24 hr). In any of these articles, the second area A2 and the third area A3 may have a strength sufficient to minimize the lateral growth of the article during application and wearing conditions, as described hereinabove, and noted by the tensile strengths of the materials used in those regions as noted below. The first area A1 comprises at least two layers of nonwoven (e.g., the illustrated first area A1 of FIG. 3 contains the inner and outer surfaces of the outer cuff 74). Other contemplated absorbent articles may comprise even more layers of materials in the first area A1, such as three layers of SMNS cuff material. The second area A2 and the third area A3 comprise three or more layers of nonwoven (e.g., the illustrated second area A2 and third area A3 of FIGS. 3A and 3B contain two layers of outer cuff 74 nonwoven and the opacity strength patch 80). The second area A2 and the third area A3 may also comprise a backsheet nonwoven 26 (also illustrated in the second area A2 and third area A3 of FIGS. 3A and 3B) for a total of four layers of nonwoven in these areas. Other contemplated absorbent articles may comprise even more layers of materials in the second area A2 and third area A3, such as three layers of SMNS cuff material in addition to the opacity strengthening patch and/or the backsheet nonwoven.

The first area A1 and at least one of the fourth area A4, located in the second waist region 38 outboard of the outer cuff 74 of the leg gasketing system, and the fifth area A5, located in the first waist region 36 outboard of the outer cuff 74 of the leg gasketing system, may be breathable in order to maximize the portion of the perimeter of the closed leg hoop which is breathable when the article is being worn by a wearer. The fourth area A4 and the fifth area A5 are longitudinally outboard of the first area A1. The fourth area A4 and the fifth area A5 are laterally outboard from the first area A1. The fourth area A4 and the fifth area A5 are also laterally outboard from the second area A2 and the third area A3, as illustrated in FIG. 1. The fourth area A4 and fifth area A5 may be both centered along a longitudinally running line that is parallel to the longitudinal centerline 100. The fourth area A4 and the second area A2 are also both centered along a laterally running line (i.e., a first line D-D) that is parallel to the lateral centerline 110. If the absorbent article being measured has separately attached ears in the second waist region 38, the first line D-D is located inboard of the longitudinally inboard edge of the separately attached ear by 10 mm. If the absorbent article being measured does not have separately attached ears, the first line D-D is located 50 mm inboard from the second waist edge 14. The fifth area A5 and the third area A3 are also both centered along a laterally running line (i.e., a second line E-E) that is parallel to the lateral centerline 110. If the absorbent article being measured has separately attached ears in the first waist region 36, the second line E-E is located inboard of the longitudinally inboard edge of the separately attached ear by 10 mm. If the absorbent article being measured does not have separately attached ears, the second line E-E is located 50 mm inboard from the first waist edge 13. The fourth area A4 and the fifth area A5 may need to be more breathable than the first area A1 because these regions may overlap each other when the article is in a closed, fastened configuration and the hip area of the wearer is prone to sweating. As with the second area A2 and the third area A3, the fourth area A4 and the fifth area A5 may be breathable to enable sweat from the hip region of the wearer to evaporate, reducing the likelihood of anhidrosis in this region. The fourth area A4 and the fifth area A5 comprise two or more layers of nonwoven (e.g., opacity strength patch 80 and backsheet nonwoven 26, as illustrated in the cross section of FIGS. 3A and 3B). Other contemplated absorbent articles may comprise even more layers of materials in the fourth area A4 and fifth area A5.

The first area A1, the second area A2, the third area A3, the fourth area A4, and the fifth area A5 may all be breathable. The WVTR of the fourth area A4 and the fifth area A5 may be at least about 4000 g/m²/24 hr and may be in the range of about 4400 to about 6000 g/m²/24 hr. The fourth area A4 and the fifth area A5 may comprise one or more nonwoven layers (e.g., the illustrated fourth area A4 and fifth area A5 of FIGS. 3A and 3B contain an opacity strengthening patch 80 and back sheet outer cover 26) to achieve the desired tactile properties and strength.

The Air Permeability of the first area A1, second area A2, the third area A3, the fourth area A4, and the fifth area A5 may be greater than about 5 m³/m²/min, or greater than about 7 m³/m²/min in order to provide sufficient air transfer to and from the skin to minimize the potential for skin over hydration. The Air Permeability of these areas may be in the range of about 5 to about 70 m³/m²/min. The Air Permeability of the first area A1 may be about 5 to about 70 m³/m²/min, or about 7 to about 70 m³/m²/min, or about 10 to about 70 m³/m²/min, or about 15 to about 30 m³/m²/min, or about 15 to about 25 m³/m²/min, or about 15 to about 20 m³/m²/min, or any numeric range contained therein. The Air Permeability of the second area A2 and third area A3 may be in the range of about 5 to about 25 m³/m²/min, or about 7 to about 25 m³/m²/min, or about 10 to about 25 m³/m²/min, or about 10 to about 20 m³/m²/min, or about 10 to about 15 m³/m²/min, or about 7 to about 15 m³/m²/min, or any numeric range contained therein. The Air Permeability of the fourth area A4 and fifth area A5 may be in the range of about 20 to about 70 m³/m²/min, or about 25 to about 70 m³/m²/min, or about 30 to about 50 m³/m²/min, or about 35 to about 45 m³/m²/min, or any numeric range contained therein.

The first area A1, the second area A2, the third area A3, the fourth area A4, and the fifth area A5 have an opacity sufficiently high to prevent or minimize the visibility of the underlying skin of the wearer when the article is being worn. The opacity of these areas may be greater than about 55. The opacity of these areas may be in the range of about 55 to about 100, or about 60 to about 90. The opacity of the first area A1 may be lower than at least one of the other regions (e.g., A2, A3, A4 and/or A5), in order to present an enhanced appearance of comfort. The opacity of the first area A1 may be about 60 to about 70, or about 62 to about 68, or about 65. The opacity of the second area A2 and third area may be about 70 to about 100, or about 75 to about 90, or about 78 to about 85, or about 80. The opacity of the fourth area A4 and fifth area A5 may be about 55 to about 70, or about 60 to about 65, or about 61. Accordingly, the opacity of the fourth area A4 and fifth area A5 may be lower than the opacity of the first area A1, which may be lower than the opacity of the second area A2 and third area A3.

The first area A1, the second area A2, the third area A3, the fourth area A4, and the fifth area A5 may have a Hydrohead Pressure (1$^{st}$ drop) and Low ST Strikethrough greater than about 20 mbar and about 10 seconds, respectively, in order to prevent inadvertent leakage of urine or feces through those portions of the article onto the wearer's clothing or into the environment.

EXAMPLES

| Product | Lot No. | Opacity % Outer Cuff | Opacity % Inner Cuff | Air Permeability $m^3/m^2/min$ Outer Cuff | Air Permeability $m^3/m^2/min$ Inner Cuff | WVTR $g/m^2/24$ hrs Outer Cuff | WVTR $g/m^2/24$ hrs Inner Cuff | Hydrohead mbar Outer Cuff | Hydrohead mbar Inner Cuff | 32 dyne Strikethrough Sec Outer Cuff | 32 dyne Strikethrough Sec Inner Cuff |
|---|---|---|---|---|---|---|---|---|---|---|---|
| Prototype N-Fiber | NA | 58.7 ± 2.2 | 37.6 ± 3.2 | 26.8 ± 5.6 | 36.9 ± 4.6 | 5905 ± 129 | 5224 ± 87 | 16.8 ± 2.1 | 12.3 ± 1.3 | 21.0 ± 3.5 | 9.2 ± 1.5 |
| Prototype SMS | NA | 65.8 ± 1.8 | 39.0 ± 1.0 | 65.6 ± 11.5 | 38.5 ± 3.8 | 5748 ± 276 | 5193 ± 145 | 16.3 ± 1.8 | 10.0 ± 1.7 | 15.6 ± 1.9 | 7.6 ± 1.4 |
| Pampers BabyDry | 0089U011390422 | 80.1 ± 0.4 | 38.8 ± 3.8 | 2.1 ± 1.0 | 56.1 ± 6.3 | 4063 ± 67 | 5252 ± 157 | >200 | 6.7 ± 0.8 | >100 | 10.1 ± 0.5 |
| Luvs | 1047U011390518 | 85.3 ± 1.2 | 36.4 ± 3.4 | 3.1 ± 1.9 | 90.2 ± 9.3 | 304 ± 144 | 5244 ± 26 | >200 | 6.5 ± 1.0 | >100 | 11.8 ± 1.4 |
| Huggies Little Movers | BI006912B | 80.1 ± 1.0 | 45.4 ± 4.2 | 2.6 ± 0.4 | 45.0 ± 15.7 | 3673 ± 190 | 5581 ± 90 | >200 | 8.3 ± 1.3 | >100 | 14.3 ± 3.5 |
| Huggies Supreme | NM1275U1F0755 | 72.7 ± 2.2 | 53.6 ± 2.3 | 4.4 ± 1.1 | 145.2 ± 23.2 | 375 ± 77 | 5688 ± 85 | >200 | 9.2 ± 1.8 | >100 | 14.6 ± 3.1 |

\* Results are expressed as the average ± one standard deviation
\* Prototype N-Fiber is a 13 gsm SMNS available from Polymer Group Inc
\* Prototype SMS is a 15 gsm SMS (Spunbonded-Meltblown-Spunbonded) nonwoven available from Fibertex under the Comfort Line

TABLE 2

Functional Properties in Locations A1-A5 of Prototype Absorbent Article

| Area Location of Absorbent Article (body-side faces liquid (or port) in all cases) | N | Air Permeability[1] $(m^3/m^2/min)$ Ave | Air Permeability[1] $(m^3/m^2/min)$ Std Dev | Hydrohead Pressure[2] (mbar) @ 1st Drop Ave | Hydrohead Pressure[2] (mbar) @ 1st Drop Std Dev | Hydrohead Pressure[2] (mbar) @ 3rd Drop Ave | Hydrohead Pressure[2] (mbar) @ 3rd Drop Std Dev | Opacity[3] Ave | Opacity[3] Std Dev | WVTR[4] (g/m2/24 hrs) Ave | WVTR[4] (g/m2/24 hrs) Std Dev | Low ST Strikethrough[5] (seconds) Ave | Low ST Strikethrough[5] (seconds) Std Dev |
|---|---|---|---|---|---|---|---|---|---|---|---|---|---|
| A1 - Left Side of Absorbent Article | 5 | 18.2 | 2.3 | 25.6 | 1.3 | 26.0 | 1.2 | 65.09 | 0.73 | 4631 | 176.8 | 13.7 | 1.3 |
| A1 - Right Side of Absorbent Article | 5 | 19.4 | 1.8 | 24.3 | 3.3 | 24.9 | 3.2 | 65.74 | 2.17 | 4783 | 210.7 | 13.1 | 2.4 |
| A2 - Left Side of Absorbent Article | 5 | 9.4 | 0.8 | 8.5 | 6.0 | 38.5 | 6.0 | 81.29 | 1.01 | 4478 | 173.8 | 52.4 | 10.6 |
| A2 - Right Side of Absorbent Article | 5 | 11.0 | 0.8 | 8.2 | 3.5 | 38.6 | 3.5 | 80.59 | 0.53 | 4554 | 235.4 | 56.7 | 10.8 |
| A3 - Left Side of Absorbent Article | 5 | 9.3 | 0.3 | 8.9 | 3.9 | 39.6 | 4.1 | 81.26 | 0.55 | 4454 | 167.9 | 44.2 | 19.2 |
| A3 - Right Side of Absorbent Article | 5 | 10.5 | 0.4 | 9.4 | 3.7 | 39.6 | 3.8 | 81.12 | 0.94 | 4149 | 173.2 | 56.5 | 9.5 |
| A4 - Left Side of Absorbent Article | 5 | 40.5 | 3.2 | 26.0 | 6.0 | 26.5 | 5.7 | 62.01 | 1.27 | 4593 | 150.9 | 11.2 | 2.4 |
| A4 - Right Side of Absorbent Article | 5 | 37.0 | 3.8 | 21.8 | 3.7 | 24.9 | 5.4 | 60.95 | 0.92 | 4592 | 102.5 | 12.4 | 1.9 |
| A5 - Left Side of Absorbent Article | 5 | 41.2 | 3.2 | 23.8 | 1.8 | 25.2 | 2.4 | 62.03 | 1.23 | 4692 | 244.8 | 10.9 | 1.9 |
| A5 - Right Side of Absorbent Article | 5 | 39.1 | 1.7 | 27.7 | 6.3 | 29.8 | 5.0 | 61.97 | 2.30 | 4531 | 161.4 | 12.6 | 1.2 |

\* The prototype absorbent article tested for the data generation tabulated in Table 2 was an absorbent article with a structure as shown in FIGS. 1-3. The leg gasketing material is a 15 gsm SMNS nonwoven available from Polymer Group Inc./Berry Plastics in Spain, the opacity strengthening patch is a 23 gsm SMMS from Guelsan in Turkey, the backsheet nonwoven is a 22 gsm quilted HESB Outer Cover from FQN in Hazleton, PA, the backsheet film is 16 gsm GOC2 poly from Clopay in Nashville, TN, and the topsheet is a 12 gsm surfactant treated SSS from Polymer Group Inc./Berry Plastics in Mooresville, NC.
[1]TexTest FX3300, SN 644.08.00, 1.47 $cm^2$ test head, 125 Pa pressure drop, ASTM D 737
[2]TexTest FX3000, SN 337.03.99, 1.47 $cm^2$ test head, distilled water, 3 mbar/min if <30 mbar, 10 mbar/min if >30 mbar, Edana 120.2
[3]HunterLab Labscan XE, SN LX16176, Y Opacity Procedure, 0.7" Port/0.5" Area View, 0° Illuminate/45° Detection, 10° Observer, XYZ Color Scale, D65 Illuminate/D65 M Illuminate
[4]WVTR Wet Cup, cups are 8 dram vials (95 mm tall) with opening of 17.8 mm, air gap is 25 mm from upper lip of vial, Lindberg Blue M oven at 38° C. for 24 hrs, Modified ASTM E 96
[5]Lister DC Strikethrough Tester, SN L5725, plate has 10 mm opening, 0.042% Triton-X-100 (ST = 32 mN/m) test liquid, pad is 5 plies of Ahlstrom grade 989, Modified WSP 70.3

TABLE 3

Functional Properties of Raw Materials Used in Prototype Absorbent Article

| Construction Material (body-side faces liquid (or port) in all cases) | N | Air Permeability[1] ($m^3/m^2/min$) Ave | Std Dev | Hydrohead Pressure[2] (mbar) @ 1st Drop Ave | Std Dev | (mbar) @ 3rd Drop Ave | Std Dev | Opacity[3] Ave | Std Dev | WVTR[4] (g/m2/ 24 hrs) Ave | Std Dev | Low ST Strikethrough[5] (seconds) Ave | Std Dev |
|---|---|---|---|---|---|---|---|---|---|---|---|---|---|
| 22 gsm backsheet nonwoven | 5 | 161.0 | 16.4 | 8.0 | 3.2 | 8.2 | 3.3 | 42.97 | 1.97 | 5839 | 941.8 | 7.0 | 0.6 |
| 15 gsm SMNS leg gasketing material 1 layer | 5 | 36.9 | 1.2 | 9.4 | 2.3 | 10.1 | 2.2 | 37.08 | 1.95 | 4799 | 204.0 | 12.2 | 1.1 |
| 15 gsm SMNS leg gasketing material 2 layers | 5 | 16.2 | 0.9 | 27.7 | 3.2 | 27.7 | 3.2 | 61.67 | 1.86 | 4779 | 252.1 | 18.6 | 1.3 |
| 23 gsm opacity strengthening patch | 5 | 52.8 | 1.8 | 13.5 | 7.4 | 13.8 | 7.3 | 36.58 | 2.54 | 4808 | 232.6 | 8.5 | 2.5 |
| 16 gsm backsheet film | 5 | 0.0 | 0.0 | >150 | n/a | >150 | n/a | 62.79 | 0.81 | 3892 | 191.5 | >1000 | n/a |
| 12 gsm topsheet | 5 | 270.8 | 56.3 | failed immediately | n/a | failed immediately | n/a | 16.49 | 2.03 | 6250 | 1807.6 | 7.6 | 0.5 |

* The 15 gsm SMNS nonwoven is available from Polymer Group Inc./Berry Plastics in Spain, the opacity strengthening patch is a 23 gsm SMMS available from Guelsan in Turkey, the backsheet nonwoven is a 22 gsm quilted HESB Outer Cover available from FQN in Hazleton, PA, the backsheet film is 16 gsm GOC2 poly available from Clopay in Nashville, TN, and the topsheet is a 12 gsm surfactant treated SSS available from Polymer Group Inc./Berry Plastics in Mooresville, NC.
[1] TexTest FX3300, SN 644.08.00, 1.47 $cm^2$ test head, 125 Pa pressure drop, ASTM D 737
[2] TexTest FX3000, SN 337.03.99, 1.47 $cm^2$ test head, distilled water, 3 mbar/min if <30 mbar, 10 mbar/min if >30 mbar, Edana 120.2
[3] HunterLab Labscan XE, SN LX16176, Y Opacity Procedure, 0.7" Port/0.5" Area View, 0° Illuminate/45° Detection, 10° Observer, XYZ Color Scale, D65 Illuminate/D65 M Illuminate
[4] WVTR Wet Cup, cups are 8 dram vials (95 mm tall) with opening of 17.8 mm, air gap is 25 mm from upper lip of vial, Lindberg Blue M oven at 38° C. for 24 hrs, Modified ASTM E 96
[5] Lister DC Strikethrough Tester, SN L5725, plate has 10 mm opening, 0.042% Triton-X-100 (ST = 32 mN/m) test liquid, pad is 5 plies of Ahlstrom grade 989, Modified WSP 70.3

TABLE 4

Strength Properties of Raw Materials Used in Prototype Absorbent Article

| Construction Material | N | Tensile[6] Load at Peak (N) Ave | Std Dev | Load at Break (N) Ave | Std Dev | Elongation at Peak (mm) Ave | Std Dev |
|---|---|---|---|---|---|---|---|
| 22 gsm backsheet nonwoven | 5 | MD 22.31 CD 10.93 | MD 1.37 CD 0.80 | MD 20.17 CD 9.87 | MD 1.26 CD 0.73 | MD 24.84 CD 40.34 | MD 2.46 CD 3.58 |
| 15 gsm SMNS leg gasketing material 1 layer | 5 | MD 15.49 CD 7.85 | MD 1.14 CD 0.92 | MD 13.98 CD 7.09 | MD 1.01 CD 0.83 | MD 27.38 CD 28.87 | MD 2.97 CD 3.61 |
| 15 gsm SMNS leg gasketing material 2 layers | 5 | MD 31.57 CD 15.03 | MD 1.82 CD 1.99 | MD 27.95 CD 12.36 | MD 1.89 CD 1.96 | MD 28.48 CD 28.62 | MD 3.30 CD 4.31 |
| 23 gsm opacity strengthening patch | 5 | MD 27.01 CD 13.93 | MD 2.58 CD 0.44 | MD 25.79 CD 12.85 | MD 3.27 CD 0.50 | MD 36.18 CD 31.87 | MD 2.34 CD 3.79 |
| 16 gsm backsheet film | 5 | MD 5.77 CD 3.07 | MD 0.5 CD 0.45 | MD 5.53 CD 2.88 | MD 0.74 CD 0.56 | MD 209.34 CD 150.66 | MD 19.80 CD 149.33 |
| 12 gsm topsheet | 5 | MD 13.94 CD 5.13 | MD 1.35 CD 0.23 | MD 11.97 CD 4.67 | MD 1.49 CD 0.21 | MD 22.08 CD 31.28 | MD 3.25 CD 3.97 |

| Construction Material | Tensile[6] Elongation at Break (mm) Ave | Std Dev | Energy to Peak (N*mm) Ave | Std Dev |
|---|---|---|---|---|
| 22 gsm backsheet nonwoven | MD 28.07 CD 42.67 | MD 1.06 CD 3.91 | MD 378.94 CD 234.96 | MD 57.38 CD 36.26 |
| 15 gsm SMNS leg gasketing material 1 layer | MD 30.83 CD 31.56 | MD 3.47 CD 4.24 | MD 304.80 CD 146.13 | MD 55.93 CD 31.76 |

TABLE 4-continued

Strength Properties of Raw Materials Used in Prototype Absorbent Article

|  |  |  |  |  |
|---|---|---|---|---|
| 15 gsm SMNS leg gasketing material 2 layers | MD 32.02 CD 35.75 | MD 2.66 CD 1.09 | MD 648.08 CD 270.18 | MD 115.98 CD 72.90 |
| 23 gsm opacity strengthening patch | MD 38.30 CD 34.80 | MD 3.25 CD 3.77 | MD 714.90 CD 296.87 | MD 108.61 CD 43.82 |
| 16 gsm backsheet film | MD 212.86 CD 177.93 | MD 17.18 CD 122.49 | MD 894.38 CD 398.45 | MD 98.81 CD 404.07 |
| 12 gsm topsheet | MD 24.53 CD 34.72 | MD 3.08 CD 3.76 | MD 215.47 CD 89.27 | MD 49.08 CD 17.25 |

[6]MTS Insight_1EL, SN 10303718C, System #40284-C with 100N load cell (model 569326-05, SN 215921); 2" gauge length, 1" wide, 100 mm/min, 100 Hz DAQ, 10% break point detection

TABLE 5

Functional Properties in Locations A1-A5 of Size 4 Pampers Cruisers

| Area Location of Absorbent Article (body-side faces liquid (or port) in all cases) | N | Air Permeability[1] (m$^3$/m$^2$/min) | | Hydrohead Pressure[2] | | | | Opacity[3] | | WVTR[4] (g/m2/ 24 hrs) | | Low ST Strikethrough[5] (seconds) | |
|---|---|---|---|---|---|---|---|---|---|---|---|---|---|
| | | | | (mbar) @ 1st Drop | | (mbar) @ 3rd Drop | | | | | | | |
| | | Ave | Std Dev | Ave | Std Dev | Ave | Std Dev | Ave | Std Dev | Ave | Std Dev | Ave | Std Dev |
| A1 - Left Side of Absorbent Article | 3 | 0.39 | 0.01 | >200 (1 fail at 65.0) | na | >200 (1 fail at 74.1) | na | 79.57 | 1.63 | 3531 | 111.2 | 529, >1000, >1000 | n/a |
| A1 - Right Side of Absorbent Article | 3 | 0.75 | 0.33 | >200 (n = 1) | na | >200 (n = 1) | na | 81.94 | 2.73 | 3438 | 107.7 | 914.0 | 27.8 |
| A2 - Left Side of Absorbent Article | 3 | 0.40 | 0.03 | >200 (n = 1) | na | >200 (n = 1) | na | 82.91 | 3.09 | 3329 | 98.1 | 615.4 | 85.2 |
| A2 - Right Side of Absorbent Article | 3 | 0.39 | 0.05 | >200 (n = 1) | na | >200 (n = 1) | na | 80.51 | 0.28 | 3303 | 178.9 | 295.2 | 6.9 |
| A3 - Left Side of Absorbent Article | 3 | 0.73 | 0.11 | >200 (n = 1) | na | >200 (n = 1) | na | 90.92 | 0.12 | 3223 | 38.5 | >1000 (n = 3) | n/a |
| A3 - Right Side of Absorbent Article | 3 | 0.66 | 0.10 | >200 (n = 1) | na | >200 (n = 1) | na | 89.21 | 2.11 | 3343 | 139.5 | >1000, 995, >1000 | n/a |
| A4 - Left Side of Absorbent Article | 3 | 0.55 | 0.04 | >200 (n = 1) | na | >200 (n = 1) | na | 75.04 | 1.19 | 292 | 32.8 | >1000 (n = 3) | n/a |
| A4 - Right Side of Absorbent Article | 3 | 0.69 | 0.16 | >200 (n = 1) | na | >200 (n = 1) | na | 74.83 | 0.66 | 231 | 118.6 | >1000 (n = 3) | n/a |
| A5 - Left Side of Absorbent Article | 3 | 101.8 | 15.0 | 3.5 | 2.2 | 3.7 | 2.0 | 63.67 | 2.98 | 4504 | 268.9 | 8.6 | 0.7 |
| A5 - Right Side of Absorbent Article | 3 | 93.6 | 7.8 | 6.8 | 3.8 | 7.7 | 4.0 | 64.53 | 0.46 | 4835 | 134.4 | 8.7 | 1.0 |

[1]TexTest FX3300, SN 644.08.00, 1.47 cm$^2$ test head, 125 Pa pressure drop, ASTM D 737
[2]TexTest FX3000, SN 337.03.99, 1.47 cm$^2$ test head, distilled water, 3 mbar/min if <30 mbar, 10 mbar/min if >30 mbar, Edana 120.2
[3]HunterLab Labscan XE, SN LX16176, Y Opacity Procedure, 0.7" Port/0.5" Area View, 0° Illuminate/45° Detection, 10° Observer, XYZ Color Scale, D65 Illuminate/D65 M Illuminate
[4]WVTR Wet Cup, cups are 8 dram vials (95 mm tall) with opening of 17.8 mm, air gap is 25 mm from upper lip of vial, Lindberg Blue M oven at 38° C. for 24 hrs, Modified ASTM E 96
[5]Lister DC Strikethrough Tester, SN L5725, plate has 10 mm opening, 0.042% Triton-X-100 (ST = 32 mN/m) test liquid, pad is 5 plies of Ahlstrom grade 989, Modified WSP 70.3

TABLE 6

Functional Properties in Locations A1-A5 of Size 4 Huggies Little Movers

| Area Location of Absorbent Article (body-side faces liquid (or port) in all cases) | N | Air Permeability[1] (m$^3$/m$^2$/min) | | Hydrohead Pressure[2] | | | | Opacity[3] | | WVTR[4] (g/m2/ 24 hrs) | | Low ST Strikethrough[5] (seconds) | |
|---|---|---|---|---|---|---|---|---|---|---|---|---|---|
| | | | | (mbar) @ 1st Drop | | (mbar) @ 3rd Drop | | | | | | | |
| | | Ave | Std Dev | Ave | Std Dev | Ave | Std Dev | Ave | Std Dev | Ave | Std Dev | Ave | Std Dev |
| A1 - Left Side of Absorbent Article | 3 | 0.80 | 0.20 | >200 (n = 1) | na | >200 (n = 1) | na | 87.17 | 1.40 | 3614 | 395.8 | >1000 (n = 1) | n/a |

TABLE 6-continued

Functional Properties in Locations A1-A5 of Size 4 Huggies Little Movers

| Area Location of Absorbent Article (body-side faces) liquid (or port) in all cases) | N | Air Permeability[1] ($m^3/m^2/min$) Ave | Std Dev | Hydrohead Pressure[2] (mbar) @ 1st Drop Ave | Std Dev | (mbar) @ 3rd Drop Ave | Std Dev | Opacity[3] Ave | Std Dev | WVTR[4] (g/m2/ 24 hrs) Ave | Std Dev | Low ST Strikethrough[5] (seconds) Ave | Std Dev |
|---|---|---|---|---|---|---|---|---|---|---|---|---|---|
| A1 - Right Side of Absorbent Article | 3 | 0.87 | 0.07 | >200 (1 fail at 100) | na | >200 (1 fail at 102) | na | 86.59 | 0.54 | 4083 | 571.1 | >1000 (n = 1) | n/a |
| A2 - Left Side of Absorbent Article | 3 | 1.3 | 0.7 | >200 (n = 1) | na | >200 (n = 1) | na | 88.24 | 2.30 | 3276 | 127.9 | 105, >1000, 620 | n/a |
| A2 - Right Side of Absorbent Article | 3 | 1.4 | 0.6 | >200 (n = 1) | na | >200 (n = 1) | na | 89.80 | 1.14 | 3283 | 425.9 | >1000 (n = 1) | n/a |
| A3 - Left Side of Absorbent Article | 3 | 0.73 | 0.13 | >200 (n = 1) | na | >200 (n = 1) | na | 89.49 | 2.90 | 3398 | 176.5 | >1000 (n = 1) | n/a |
| A3 - Right Side of Absorbent Article | 3 | 0.64 | 0.12 | >200 (n = 1) | na | >200 (n = 1) | na | 87.74 | 3.68 | 3268 | 818.0 | 725, >1000, >1000 | n/a |
| A4 - Left Side of Absorbent Article | 3 | 0.55 | 0.02 | >200 (n = 1) | na | >200 (n = 1) | na | 77.59 | 0.91 | 370 | 60.4 | >1000 (n = 1) | n/a |
| A4 - Right Side of Absorbent Article | 3 | 0.61 | 0.06 | >200 (n = 1) | na | >200 (n = 1) | na | 76.69 | 1.89 | 348 | 17.0 | >1000 (n = 1) | n/a |
| A5 - Left Side of Absorbent Article | 3 | 0.70 | 0.30 | >200 (n = 1) | na | >200 (n = 1) | na | 87.59 | 1.27 | 3299 | 173.5 | 599, >1000, >1000 | n/a |
| A5 - Right Side of Absorbent Article | 3 | 0.59 | 0.16 | >200 (n = 1) | na | >200 (n = 1) | na | 83.83 | 6.34 | 3445 | 37.4 | >1000 (n = 1) | n/a |

[1]TexTest FX3300, SN 644.08.00, 1.47 cm² test head, 125 Pa pressure drop, ASTM D 737
[2]TexTest FX3000, SN 337.03.99, 1.47 cm² test head, distilled water, 3 mbar/min if <30 mbar, 10 mbar/min if >30 mbar, Edana 120.2
[3]HunterLab Labscan XE, SN LX16176, Y Opacity Procedure, 0.7" Port/0.5" Area View, 0° Illuminate/45° Detection, 10° Observer, XYZ Color Scale, D65 Illuminate/D65 M Illuminate
[4]WVTR Wet Cup, cups are 8 dram vials (95 mm tall) with opening of 17.8 mm, air gap is 25 mm from upper lip of vial, Lindberg Blue M oven at 38° C. for 24 hrs, Modified ASTM E 96
[5]Lister DC Strikethrough Tester, SN L5725, plate has 10 mm opening, 0.042% Triton-X-100 (ST = 32 mN/m) test liquid, pad is 5 plies of Ahlstrom grade 989, Modified WSP 70.3

TABLE 7

Functional Properties in Locations A1-A5 of Size 4 Luvs

| Area Location of Absorbent Article (body-side faces) liquid (or port) in all cases) | N | Air Permeability[1] ($m^3/m^2/min$) Ave | Std Dev | Hydrohead Pressure[2] (mbar) @ 1st Drop Ave | Std Dev | (mbar) @ 3rd Drop Ave | Std Dev | Opacity[3] Ave | Std Dev | WVTR[4] (g/m2/ 24 hrs) Ave | Std Dev | Low ST Strikethrough[5] (seconds) Ave | Std Dev |
|---|---|---|---|---|---|---|---|---|---|---|---|---|---|
| A1 - Left Side of Absorbent Article | 3 | 1.2 | 0.3 | >200 (n = 1) | na | >200 (n = 1) | na | 73.86 | 0.81 | 248 | 10.0 | >1000 (n = 1) | n/a |
| A1 - Right Side of Absorbent Article | 3 | 1.5 | 0.8 | >200 (n = 1) | na | >200 (n = 1) | na | 73.46 | 1.72 | 216 | 15.0 | >1000 (n = 1) | n/a |
| A2 - Left Side of Absorbent Article | 3 | 1.7 | 0.6 | >200 (n = 1) | na | >200 (n = 1) | na | 74.29 | 0.83 | 261 | 11.2 | >1000 (n = 1) | n/a |
| A2 - Right Side of Absorbent Article | 3 | 1.3 | 0.6 | >200 (n = 1) | na | >200 (n = 1) | na | 78.36 | 4.69 | 224 | 29.6 | >1000 (n = 1) | n/a |
| A3 - Left Side of Absorbent Article | 3 | 1.4 | 0.7 | >200 (n = 1) | na | >200 (n = 1) | na | 87.74 | 1.05 | 342 | 43.1 | >1000 (n = 1) | n/a |
| A3 - Right Side of Absorbent Article | 3 | 0.84 | 0.11 | >200 (1 fail at 49.5) | na | >200 (1 fail at 70.0) | na | 89.57 | 1.98 | 401 | 105.8 | >1000 (n = 1) | n/a |
| A4 - Left Side of Absorbent Article | 3 | 0.54 | 0.19 | >200 (n = 1) | na | >200 (n = 1) | na | 75.33 | 0.62 | 286 | 23.4 | >1000 (n = 1) | n/a |
| A4 - Right Side of Absorbent Article | 3 | 0.62 | 0.10 | >200 (n = 1) | na | >200 (n = 1) | na | 75.27 | 1.07 | 272 | 13.5 | >1000 (n = 1) | n/a |

TABLE 7-continued

Functional Properties in Locations A1-A5 of Size 4 Luvs

| Area Location of Absorbent Article (body-side faces liquid (or port) in all cases) | N | Air Permeability[1] (m³/m²/min) | | Hydrohead Pressure[2] | | | | Opacity[3] | | WVTR[4] (g/m2/ 24 hrs) | | Low ST Strikethrough[5] (seconds) | |
|---|---|---|---|---|---|---|---|---|---|---|---|---|---|
| | | | | (mbar) @ 1st Drop | | (mbar) @ 3rd Drop | | | | | | | |
| | | Ave | Std Dev | Ave | Std Dev | Ave | Std Dev | Ave | Std Dev | Ave | Std Dev | Ave | Std Dev |
| A5 - Left Side of Absorbent Article | 3 | 26.7 | 1.7 | 10.2 | 6.3 | 14.0 | 9.0 | 60.60 | 2.57 | 4765 | 178.0 | 15.5 | 1.9 |
| A5 - Right Side of Absorbent Article | 3 | 25.6 | 0.6 | 12.5 | 8.8 | 13.5 | 8.0 | 57.94 | 2.08 | 4758 | 349.9 | 15.9 | 1.8 |

[1]TexTest FX3300, SN 644.08.00, 1.47 cm² test head, 125 Pa pressure drop, ASTM D 737
[2]TexTest FX3000, SN 337.03.99, 1.47 cm² test head, distilled water, 3 mbar/min if <30 mbar, 10 mbar/min if >30 mbar, Edana 120.2
[3]HunterLab Labscan XE, SN LX16176, Y Opacity Procedure, 0.7" Port/0.5" Area View, 0° Illuminate/45° Detection, 10° Observer, XYZ Color Scale, D65 Illuminate/D65 M Illuminate
[4]WVTR Wet Cup, cups are 8 dram vials (95 mm tall) with opening of 17.8 mm, air gap is 25 mm from upper lip of vial, Lindberg Blue M oven at 38° C. for 24 hrs, Modified ASTM E 96
[5]Lister DC Strikethrough Tester, SN L5725 plate has 10 mm opening, 0.042% Triton-X-100 (ST = 32 mN/m) test liquid, pad is 5 plies of Ahlstrom grade 989, Modified WSP 70.3

Test Methods:
Opacity Method

Opacity is measured using a 0° illumination/45° detection, circumferential optical geometry, spectrophotometer with a computer interface such as the HunterLab Lab Scan XE running Universal Software (available from Hunter Associates Laboratory Inc., Reston, Va.) or equivalent instrument. Instrument calibration and measurements are made using the standard white and black calibration plates provided by the vendor. All testing is performed in a room maintained at 23±2° C. and 50±2% relative humidity.

The spectrophotometer is conFIG.d for the XYZ color scale, D65 illuminant, 10° standard observer, with UV filter set to nominal. The instrument is standardized according to the manufacturer's procedures using the 0.7 inch port size and 0.5 inch area view. After calibration, the software is set to the Y opacity procedure which prompts the operator to cover the sample with either the white or black calibration tile during the measurement.

Articles are pre-conditioned at 23° C.±2 C.° and 50%±2% relative humidity for two hours prior to testing. To obtain a specimen, the article is stretched flat on a bench, body facing surface upward, and the total longitudinal length of the article is measured. A testing site on the inner and outer cuffs is selected at the longitudinal midpoint of the article. Using scissors, a test specimen is cut 60 mm long by the entire height of the inner cuff centered at the longitudinal midpoint of the left cuff. Next, a second test specimen is cut, this time from the outer cuff, 60 mm long by the entire height of the outer cuff, centered at the longitudinal midpoint of the left outer cuff. In like fashion, inner and outer cuff specimens are prepared from the cuffs on the right side of the article.

The specimen is placed over the measurement port. The specimen should completely cover the port with the surface corresponding to the inner-facing surface of the cuff directed toward the port. The specimen is gently extended until taut in its longitudinal direction so that the cuff lies flat against the port plate. Adhesive tape is applied to secure the cuff to the port plate in its extended state for testing. Tape should not cover any portion of the measurement port. The specimen is then covered with the white standard plate. A reading is taken, then the white tile is removed and replaced with the black standard tile without moving the specimen. A second reading is taken, and the opacity is calculated as follows:

$$\text{Opacity} = (Y \text{ value}_{(black\ backing)} / Y \text{ value}_{(white\ backing)}) \times 100$$

Specimens from five identical articles (10 inner cuff (5 left and 5 right) and 10 outer cuff (5 left and 5 right)) are analyzed and their opacity results recorded. The average opacity for the inner cuffs and the outer cuffs are calculated and report separately, each to the nearest 0.01%.

Water Vapor Transmission Rate Method

Water Vapor Transmission Rate (WVTR) is measured using the wet cup approach. A cylindrical cup is filled with water, maintaining a constant headspace between the water surface and a specimen sealed over the cup's upper opening. The vapor loss is measured gravimetrically after heating the assembled cup for a specified time in an oven. All testing is performed in a room maintained at 23° C.±2 C.° and 50%±2% relative humidity.

Articles are preconditioned at 23° C.±2 C.° and 50%±2% relative humidity for two hours prior to testing. The article stretched flat on a bench, body facing surface upward, and the total longitudinal length of the article is measured. A testing site on the inner and outer cuffs is selected at the longitudinal midpoint of the article. Using scissors, a test specimen is cut 60 mm long by the entire height of the inner cuff centered at the longitudinal midpoint of the left cuff. Next, a second test specimen is cut, this time from the outer cuff, 60 mm long by the entire height of the outer cuff, centered at the longitudinal midpoint of the left outer cuff. In like fashion, inner and outer cuff specimens from the cuffs on the right side of the article are prepared. For measuring WVTR at specific locations on the absorbent article (e.g., A1, A2, A3, A4 and A5), a sample should be cut from the article, ensuring that all layers of the absorbent article are present in the sample at the particular location being tested.

Glass straight walled, cylindrical vials, 95 mm tall with a 17.8 mm internal diameter at the opening are used as WVTR test vials. Each test vial is filled with distilled water accurately to a level 25.0 mm±0.1 mm from the upper lip of the vial's opening. The specimen is placed, inner-facing surface of the cuff downward, over the vial's opening. The specimen is gently pulled taut and secured around the vial's circumference with an elastic band. The specimen is further sealed by wrapping Teflon tape around the vial's circumference. A preferred Teflon tape is a thread sealant tape 0.25" wide available from McMaster Carr (cat. No. 4591K11) or equivalent. The Teflon tape is applied up to the top edge of the vial but should not cover any portion of the vial's opening. The mass of the vial assembly (vial+specimen+sealing tape) is weighed to the nearest 0.0001 gram. This is the starting mass.

The vial assemblies are placed upright in a mechanical convection oven (e.g. Lindberg/BlueM oven available from ThermoScientific or equivalent) maintained at 38±1° C. for 24 hours, taking care to avoid contact between the water in the vials and the specimens. After 24 hours has elapsed, the vial assemblies are removed from the oven and allowed to come to room temperature. The mass of each vial assembly is measured to the nearest 0.0001 gram. This is the final mass.

The WVTR is calculated using the following equation:

WVTR(g/m$^2$/24 hrs)=([starting mass (g)–final mass (g)]/surface area (m$^2$))/24 hrs Specimens from five identical articles (10 inner cuff (5 left and 5 right) and 10 outer cuff (5 left and 5 right)) are analyzed and their WVTR results recorded. The average WVTR for the inner cuffs and the outer cuffs are each reported separately to the nearest 1 g/m$^2$/24 hrs.

Air Permeability Test

Air permeability is tested using a TexTest FX3300 Air Permeability Tester (available from Advanced Testing Instruments, Greer, S.C.) with a custom made 1 cm$^2$ circular aperture (also available from Advanced Testing Instruments) or equivalent instrument. The instrument is calibrated according to the manufacturer's procedures. All testing is performed in a room maintained at 23° C.±2 C.° and 50%±2% relative humidity.

The articles are pre-conditioned at 23° C.±2 C.° and 50%±2% relative humidity for two hours prior to testing. To obtain a specimen, the article is stretched flat on a bench, body facing surface upward, and the total longitudinal length of the article is measured. A testing site on the inner and outer cuffs is selected at the longitudinal midpoint of the article. Using scissors, a test specimen is cut 60 mm long by the entire height of the inner cuff centered at the longitudinal midpoint of the left cuff. Next, a second test specimen is cut, this time from the outer cuff, 60 mm long by the entire height of the outer cuff, centered at the longitudinal midpoint of the left outer cuff. In like fashion, inner and outer cuff specimens are prepared from the cuffs on the right side of the article.

The specimen is centered over the measurement port. The specimen should completely cover the port with the surface corresponding to the inward-facing surface of the cuff directed toward the port. The specimen is gently extended in its longitudinal direction until taut so that the cuff lies flat across the port. Adhesive tape is applied to secure the cuff across the port in its extended state for testing. Tape should not cover any portion of the measurement port. The test pressure is set to allow air to pass through the specimen. For non-woven cuffs the pressure is typically set for 125 Pa and for cuffs containing films typically 2125 Pa is used. The sample ring is closed and the measuring range is adjusted until the range indicator shows green to indicate that the measurement is within the accepted limits of the instrument. The air permeability is recorded to the nearest 0.1 m$^3$/m$^2$/min.

Hydrostatic Head Test

Hydrostatic head is tested using a TexTest FX3000 Hydrostatic Head Tester (available from Advanced Testing Instruments, Greer, S.C.) with a custom made 1.5 cm$^2$ circular measurement port (also available from Advanced Testing Instruments). Two annular sleeve rings, the same dimensions as the gaskets around the measurement ports, are cut from the standard protective sleeves for fine nonwovens (part FX3000-NWH, available from Advanced Testing Instruments). The sleeve rings are then adhered with two-sided adhesive tape to the sample facing surfaces of the upper and lower gaskets of the TexTest instrument to protect the specimen during clamping. Standardize the instrument according to the manufacturer's procedures. All testing is performed in a room maintained at 23° C.±2 C.° and about 50%±2% relative humidity.

Precondition the articles at about 23° C.±2 C.° and about 50%±2% relative humidity for two hours prior to testing. To obtain a specimen, lay the article stretched flat on a bench, body facing surface upward, and measure the total longitudinal length of the article. Select a testing site on the inner and outer cuffs, at the longitudinal midpoint of the article. Using scissors cut a test specimen 70 mm long by the entire height of the inner cuff centered at the longitudinal midpoint of the left cuff. Next cut a second test specimen, this time from the outer cuff, 70 mm long by the entire height of the outer cuff, centered at the longitudinal midpoint of the left outer cuff. In like fashion, prepare inner and outer cuff specimens from the cuffs on the right side of the article.

Place the specimen centered over the port of the upper test head. The specimen should completely cover the port with the surface corresponding to the outward-facing surface of the cuff directed toward the port (inner-facing surface will then be facing the water). Gently extend the specimen taut in its longitudinal direction so that the cuff lies flat against the upper test plate. Adhesive tape is applied to secure the cuff to the test plate in its extended state for testing. Tape should not cover any portion of the measurement port.

Fill the TexTest syringe with distilled water, adding the water through the measurement port of the lower test plate. The water level should be filled to the top of the lower gasket. Mount the upper test head onto the instrument and lower the test head to make a seal around the specimen. The test speed is set to 3 mbar/min for samples that have a hydrostatic head of 50 mbar or less and a speed of 60 mbar/min for samples with a hydrostatic head above 50 mbar. Start the test and observe the specimen surface to detect water droplets penetrating the surface. The test is terminated when one drop is detected on the surface of the specimen or the pressure exceeds 200 mbar. Record the pressure to the nearest 0.5 mbar or record as >200 mbar if there was no penetration detected.

A total of five identical articles (10 inner cuff and 10 outer cuff specimens) are analyzed and their hydrostatic head results recorded. Calculate and report the average hydrostatic head for the inner cuffs and the outer cuffs and report each to the nearest 0.1 mbar.

Low Surface Tension Fluid Strikethrough Time Test

The low surface tension fluid strikethrough time test is used to determine the amount of time it takes a specified quantity of a low surface tension fluid, discharged at a prescribed rate, to fully penetrate a sample of a web (and other comparable barrier materials) which is placed on a reference absorbent pad.

For this test, the reference absorbent pad is 5 plies of Ahlstrom grade 989 filter paper (10 cm×10 cm) and the test fluid is a 32 mN/m low surface tension fluid.

This test is designed to characterize the low surface tension fluid strikethrough performance (in seconds) of webs intended to provide a barrier to low surface tension fluids, such as runny BM, for example.

Lister Strikethrough Tester: The instrumentation is like described in EDANA ERT 153.0-02 section 6 with the following exception: the strike-through plate has a star-shaped orifice of 3 slots angled at 60 degrees with the narrow slots having a 10.0 mm length and a 1.2 mm slot width. This equipment is available from Lenzing Instruments (Austria)

and from W. Fritz Metzger Corp (USA). The unit needs to be set up such that it does not time out after 100 seconds.

Reference Absorbent Pad: Ahlstrom Grade 989 filter paper, in 10 cm×10 cm areas, is used. The average strikethrough time is 3.3+0.5 seconds for 5 plies of filter paper using the 32 mN/m test fluid and without the web sample. The filter paper may be purchased from Empirical Manufacturing Company, Inc. (EMC) 7616 Reinhold Drive Cincinnati, Ohio 45237.

Test Fluid: The 32 mN/m surface tension fluid is prepared with distilled water and 0.42+/−0.001 g/liter Triton-X 100. All fluids are kept at ambient conditions.

Electrode-Rinsing Liquid: 0.9% sodium chloride (CAS 7647-14-5) aqueous solution (9 g NaCl per 1 L of distilled water) is used.

Test Procedure

All testing is performed in a room maintained at about 23° C.±2 C.° and about 50%±2% relative humidity. The Ahlstrom filter paper and test articles are conditioned in this controlled environment for 24 hours and 2 hours before testing.

Ensure that the surface tension is 32 mN/m+/−1 mN/m. Otherwise remake the test fluid.

Prepare the 0.9% NaCl aqueous electrode rinsing liquid.

Ensure that the strikethrough target (3.3+/−0.5 seconds) for the Reference Absorbent Pad is met by testing 5 plies with the 32 mN/m test fluid as follows:

Neatly stack 5 plies of the Reference Absorbent Pad onto the base plate of the strikethrough tester.

Place the strikethrough plate over the 5 plies and ensure that the center of the plate is over the center of the paper. Center this assembly under the dispensing funnel.

Ensure that the upper assembly of the strikethrough tester is lowered to the pre-set stop point.

Ensure that the electrodes are connected to the timer.

Turn the strikethrough tester "on" and zero the timer.

Using the 5 mL fixed volume pipette and tip, dispense 5 mL of the 32 mN/m test fluid into the funnel.

Open the magnetic valve of the funnel (by depressing a button on the unit, for example) to discharge the 5 mL of test fluid. The initial flow of the fluid will complete the electrical circuit and start the timer. The timer will stop when the fluid has penetrated into the Reference Absorbent Pad and fallen below the level of the electrodes in the strikethrough plate.

Record the time indicated on the electronic timer.

Remove the test assembly and discard the used Reference Absorbent Pad. Rinse the electrodes with the 0.9% NaCl aqueous solution to "prime" them for the next test. Dry the depression above the electrodes and the back of the strikethrough plate, as well as wipe off the dispenser exit orifice and the bottom plate or table surface upon which the filter paper is laid.

Repeat this test procedure for a minimum of 3 replicates to ensure the strikethrough target of the Reference Absorbent Pad is met. If the target is not met, the Reference Absorbent Pad may be out of spec and should not be used.

After the Reference Absorbent Pad performance has been verified, nonwoven web samples may be tested.

Precondition the test articles at about 23° C.±2 C.° and about 50%±2% relative humidity for two hours prior to testing. To obtain a specimen, lay the article stretched flat on a bench, body facing surface upward, and measure the total longitudinal length of the article.

Select a testing site on the inner and outer cuffs, at the longitudinal midpoint of the article. Using scissors cut a test specimen 70 mm long by the entire height of the inner cuff centered at the longitudinal midpoint of the left cuff. Next cut a second test specimen, this time from the outer cuff, 70 mm long by the entire height of the outer cuff, centered at the longitudinal midpoint of the left outer cuff. In like fashion, prepare inner and outer cuff specimens from the cuffs on the right side of the article.

Place the specimen centered over the port of the strike through plate. The specimen should completely cover the port with the surface corresponding to the body-facing surface of the cuff directed toward the port. Gently extend the specimen taut in its longitudinal direction so that the cuff lies flat against the upper test plate. Adhesive tape is applied to secure the cuff to the test plate in its extended state for testing. Tape should not cover any portion of the measurement port.

Ensure that the upper assembly of the strikethrough tester is lowered to the pre-set stop point.

Ensure that the electrodes are connected to the timer. Turn the strikethrough tester "on" and zero the timer.

Run as described above.

Repeat this procedure for three articles. Average the six values and report as the 32 mN/m low surface tension strikethrough time to the nearest 0.1 seconds.

Packaging:

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 12:
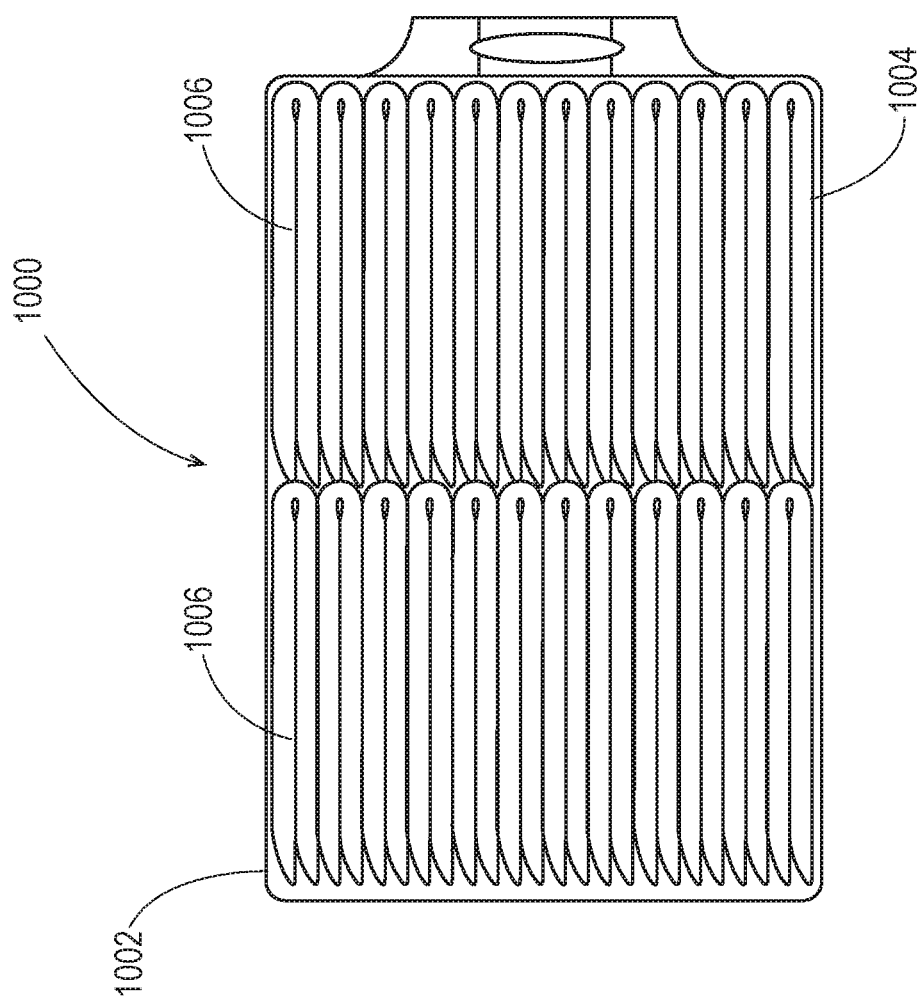
FIG. 12 is a schematic cross sectional view of a package of absorbent articles as detailed herein.

FIG. 12 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 12). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

EXAMPLES

A. A disposable absorbent article for wearing about the lower torso of a wearer, the disposable absorbent article comprising: a first waist region, a second waist region, a crotch region disposed between the first and second waist regions; a first waist edge and a second waist edge; and a first longitudinal edge and a second longitudinal edge; wherein the disposable absorbent article comprises a chassis comprising:
  1.) a topsheet;
  2.) a backsheet; and
  3.) an absorbent core disposed between the topsheet and the backsheet;
  wherein the disposable absorbent article further comprises a leg gasketing system;
  wherein the leg gasketing system comprises a web of material forming an inner cuff and an outer cuff;
  wherein the inner cuff comprises an inner cuff folded edge and an inner cuff material edge and the outer cuff comprises an outer cuff folded edge and an outer cuff material edge, such that the web of material is folded laterally inward to form the outer cuff folded edge and folded laterally outward to form the inner cuff folded edge;
  wherein the disposable absorbent article comprises a first area located in the crotch region, a second area located in the second waist region, a third area located in the first waist region, a fourth area, and a fifth area, wherein the first area of the disposable absorbent article is more breathable than both the second area and the third area, and wherein the first area of the disposable absorbent article is less breathable than both the fourth area and the fifth area.

B. The disposable absorbent article of Paragraph A, wherein the fourth area located in the second waist region, and the fifth area located in the first waist region, wherein the second area is laterally inboard of the fourth area, and the third area is laterally inboard of the fifth area.

C. The disposable absorbent article of any of Paragraphs A-B, wherein the first area is located on the outer cuff and centered on a lateral centerline.

D. The disposable absorbent article of any of Paragraphs A-C, wherein the locations of the second area and the fourth area are centered on a first line running in the lateral direction that is parallel to a lateral centerline, and the locations of the third area and the fifth area are centered on a second line running in the lateral direction that is parallel to the lateral centerline.

E. The disposable absorbent article of any of Paragraphs A-D, wherein the locations of the first area, the second area and the third area are centered on a line running in the longitudinal direction that is parallel to a longitudinal centerline.

F. The disposable absorbent article of any of Paragraphs A-E, wherein the locations of the fourth area and the fifth area are centered on a line running in the longitudinal direction that is parallel to a longitudinal centerline.

G. The disposable absorbent article of any one of Paragraphs A-F, wherein the first area has an air permeability of about 15 to about 25 $m^3/m^2/min$.

H. The disposable absorbent article of any one of Paragraphs A-G, wherein the second area and the third area have an air permeability of about 5 to about 15 $m^3/m^2/min$.

I. The disposable absorbent article of any one of Paragraphs A-H, wherein the fourth area and the fifth area have an air permeability of about 25 to about 70 $m^3/m^2/min$.

J. A disposable absorbent article for wearing about the lower torso of a wearer, the disposable absorbent article comprising: a first waist region, a second waist region, a crotch region disposed between the first and second waist regions; a first waist edge and a second waist edge; and a first longitudinal edge and a second longitudinal edge; wherein the disposable absorbent article comprises a chassis comprising:
  1.) a topsheet;
  2.) a backsheet; and
  3.) an absorbent core disposed between the topsheet and the backsheet;
  wherein the disposable absorbent article further comprises a leg gasketing system;
  wherein the leg gasketing system comprises a web of material forming an inner cuff and an outer cuff;
  wherein the inner cuff comprises an inner cuff folded edge and an inner cuff material edge and the outer cuff comprises an outer cuff folded edge and an outer cuff material edge, such that the web of material is folded laterally inward to form the outer cuff folded edge and folded laterally outward to form the inner cuff folded edge;

wherein the disposable absorbent article comprises a first area located in the crotch region, a second area located in the second waist region, a third area located in the first waist region, a fourth area, and a fifth area, wherein the first area of the disposable absorbent article has an air permeability of about 15 to about 25 m$^3$/m$^2$/min, and the second and third areas of the disposable absorbent article have an air permeability of about 7 to about 15 m$^3$/m$^2$/min, and the fourth and fifth areas of the disposable absorbent article have an air permeability of about 25 to about 70 m$^3$/m$^2$/min.

K. The disposable absorbent article of Paragraph J, wherein the first area has a WVTR range of about 4000 to about 6000 g/m$^2$/24 hr L. The disposable absorbent article of any of Paragraphs J-K, wherein the third area and the fourth area have a WVTR range of about 3800 to about 5500 g/m$^2$/24 hr.

M. The disposable absorbent article of any of Paragraphs J-L, wherein the fourth area and the fifth area have a WVTR range of about 4400 to about 6000 g/m$^2$/24 hr.

N. The disposable absorbent article of any of Paragraphs J-M, wherein the first area, second area, third area, fourth area and the fifth area have an opacity range of about 55 to about 100.

O. The disposable absorbent article of any of Paragraphs J-N, wherein the first area has an opacity range of about 60 to about 70.

P. The disposable absorbent article of any of Paragraphs J-O, wherein the second area and third area have an opacity range of about 75 to about 90.

Q. The disposable absorbent article of any of Paragraphs J-P, wherein the fourth area and fifth area have an opacity range of about 55 to about 70.

R. The disposable absorbent article of any of Paragraphs J-Q, wherein the first area has a higher opacity than the fourth or fifth areas, and the first area has a lower opacity than the second or third areas.

S. A disposable absorbent article for wearing about the lower torso of a wearer, the disposable absorbent article comprising: a first waist region, a second waist region, a crotch region disposed between the first and second waist regions; a first waist edge and a second waist edge; and a first longitudinal edge and a second longitudinal edge; wherein the disposable absorbent article comprises a chassis comprising:

1.) a topsheet;
2.) a backsheet; and
3.) an absorbent core disposed between the topsheet and the backsheet;

wherein the disposable absorbent article further comprises a leg gasketing system;

wherein the leg gasketing system comprises a web of material forming an inner cuff and an outer cuff;

wherein the inner cuff comprises an inner cuff folded edge and an inner cuff material edge and the outer cuff comprises an outer cuff folded edge and an outer cuff material edge, such that the web of material is folded laterally inward to form the outer cuff folded edge and folded laterally outward to form the inner cuff folded edge;

wherein the disposable absorbent article comprises a first area located in the crotch region, a second area located in the second waist region, a third area located in the first waist region, a fourth area, and a fifth area, wherein a cross section of the first area of the disposable absorbent article contains less layers of material than both a cross section of the second area of the disposable absorbent article and a cross section of the third area of the disposable absorbent article.

T. The disposable absorbent article of Paragraph S, wherein the fourth area located in the second waist region and the fifth area located in the first waist region, wherein the cross section of the first area contains two layers of material.

U. The disposable absorbent article of any of Paragraphs S-T, wherein the cross section of the second area and the cross section of the third area each contain at least three layers of material.

V. The disposable absorbent article of any of Paragraphs S-V, wherein a cross section of the fourth area and a cross section of the fifth area each contain at least two layers of material.

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article for wearing about the lower torso of a wearer, the disposable absorbent article comprising: a first waist region, a second waist region, a crotch region disposed between the first and second waist regions; a first waist edge and a second waist edge; and a first longitudinal edge and a second longitudinal edge; wherein the disposable absorbent article comprises a chassis comprising:

1) a topsheet;
2) a backsheet; and
3) an absorbent core disposed between the topsheet and the backsheet;

wherein the disposable absorbent article further comprises a leg gasketing system;

wherein the leg gasketing system comprises a web of material forming an inner cuff and an outer cuff;

wherein the inner cuff comprises an inner cuff folded edge and an inner cuff material edge and the outer cuff comprises an outer cuff folded edge and an outer cuff material edge, such that the web of material is folded laterally inward to form the outer cuff folded edge and folded laterally outward to form the inner cuff folded edge;

wherein the disposable absorbent article comprises a first area located in the crotch region, a second area located in the second waist region, a third area located in the first waist region, a fourth area, and a fifth area, wherein the first area of the disposable absorbent article is more breathable than each of the second area and the third area, wherein the first area, the second area, the third area, the fourth area, and the fifth area are all located laterally outboard of the absorbent core, and wherein the first area of the disposable absorbent article is less breathable than each of the fourth area and the fifth area.

2. The disposable absorbent article of claim 1, wherein the fourth area located in the second waist region, and the fifth area located in the first waist region, wherein the second area is laterally inboard of the fourth area, and the third area is laterally inboard of the fifth area.

3. The disposable absorbent article of claim 1, wherein the first area is located on the outer cuff and centered on a lateral centerline.

4. The disposable absorbent article of claim 2, wherein the locations of the second area and the fourth area are centered on a first line running in the lateral direction that is parallel to a lateral centerline, and the locations of the third area and the fifth area are centered on a second line running in the lateral direction that is parallel to the lateral centerline.

5. The disposable absorbent article of claim 1, wherein the locations of the first area, the second area and the third area are centered on a line running in the longitudinal direction that is parallel to a longitudinal centerline.

6. The disposable absorbent article of claim 2, wherein the locations of the fourth area and the fifth area are centered on a line running in the longitudinal direction that is parallel to a longitudinal centerline.

7. The disposable absorbent article of claim 1, wherein the first area has an air permeability of about 15 to about 25 $m^3/m^2/min$.

8. The disposable absorbent article of claim 1, wherein the second area and the third area have an air permeability of about 5 to about 15 $m^3/m^2/min$.

9. The disposable absorbent article of claim 1, wherein the fourth area and the fifth area have an air permeability of about 25 to about 70 $m^3/m^2/min$.

10. A disposable absorbent article for wearing about the lower torso of a wearer, the disposable absorbent article comprising: a first waist region, a second waist region, a crotch region disposed between the first and second waist regions; a first waist edge and a second waist edge; and a first longitudinal edge and a second longitudinal edge; wherein the disposable absorbent article comprises a chassis comprising:
1) a topsheet;
2) a backsheet; and
3) an absorbent core disposed between the topsheet and the backsheet;
wherein the disposable absorbent article further comprises a leg gasketing system;
wherein the leg gasketing system comprises a web of material forming an inner cuff and an outer cuff;
wherein the inner cuff comprises an inner cuff folded edge and an inner cuff material edge and the outer cuff comprises an outer cuff folded edge and an outer cuff material edge, such that the web of material is folded laterally inward to form the outer cuff folded edge and folded laterally outward to form the inner cuff folded edge;

wherein the disposable absorbent article comprises a first area located in the crotch region, a second area located in the second waist region, a third area located in the first waist region, a fourth area, and a fifth area, wherein the first area, the second area, the third area, the fourth area, and the fifth area are all located laterally outboard of the absorbent core, wherein the first area of the disposable absorbent article has an air permeability of about 15 to about 25 $m^3/m^2/min$, and the second and third areas of the disposable absorbent article have an air permeability of about 7 to about 15 $m^3/m^2/min$, and the fourth and fifth areas of the disposable absorbent article have an air permeability of about 25 to about 70 $m^3/m^2/min$.

11. The disposable absorbent article of claim 10, wherein the first area has a WVTR range of about 4000 to about 6000 $g/m^2/24$ hr, the second area and the third area have a WVTR range of about 3800 to about 5500 $g/m^2/24$ hr, and the fourth area and the fifth area have a WVTR range of about 4400 to about 6000 $g/m^2/24$ hr.

12. The disposable absorbent article of claim 10, wherein the first area, second area, third area, fourth area and the fifth area have an opacity range of about 55 to about 100.

13. The disposable absorbent article of claim 10, wherein the first area has an opacity range of about 60 to about 70.

14. The disposable absorbent article of claim 10, wherein the second area and third area have an opacity range of about 75 to about 90.

15. The disposable absorbent article of claim 10, wherein the fourth area and fifth area have an opacity range of about 55 to about 70.

16. The disposable absorbent article of claim 10, wherein the first area has a higher opacity than the fourth or fifth areas, and the first area has a lower opacity than the second or third areas.

17. A disposable absorbent article for wearing about the lower torso of a wearer, the disposable absorbent article comprising: a first waist region, a second waist region, a crotch region disposed between the first and second waist regions; a first waist edge and a second waist edge; and a first longitudinal edge and a second longitudinal edge; wherein the disposable absorbent article comprises a chassis comprising:
1) a topsheet;
2) a backsheet; and
3) an absorbent core disposed between the topsheet and the backsheet;
wherein the disposable absorbent article further comprises a leg gasketing system;
wherein the leg gasketing system comprises a web of material forming an inner cuff and an outer cuff;
wherein the inner cuff comprises an inner cuff folded edge and an inner cuff material edge and the outer cuff comprises an outer cuff folded edge and an outer cuff material edge, such that the web of material is folded laterally inward to form the outer cuff folded edge and folded laterally outward to form the inner cuff folded edge; and
wherein the disposable absorbent article comprises a first area located in the crotch region, a second area located in the second waist region, a third area located in the first waist region, a fourth area, and a fifth area, wherein the first area, the second area, the third area, the fourth area, and the fifth area are all located laterally outboard of the absorbent core, wherein a cross section of the first area of the disposable absorbent article contains less layers of material than each of a cross section of the second area of the disposable absorbent article and a cross section of the third area of the disposable absorbent article.

18. The disposable absorbent article of claim 17, wherein the fourth area located in the second waist region and the fifth area located in the first waist region, wherein the cross section of the first area contains two layers of material.

19. The disposable absorbent article of claim 17, wherein the cross section of the second area and the cross section of the third area each contain at least three layers of material.

20. The disposable absorbent article of claim 17, wherein a cross section of the fourth area and a cross section of the fifth area each contain at least two layers of material.

21. The disposable absorbent article of claim 17, wherein at least a portion of the web of material between the outer cuff folded edge and the outer cuff material edge is attached to the chassis in the first waist region, the second waist region and the crotch region; and at least a portion of the web of material between the inner cuff folded edge and the outer cuff folded edge is attached to the web of material between the outer cuff folded edge and the outer cuff material edge in the crotch region and the first waist region; and the web of material between the inner cuff folded edge and the outer cuff folded edge is unattached to the web of material between the outer cuff folded edge and the outer cuff material edge in at least a portion of the second waist region, forming a leg gasketing system pocket with an opening on an inboard longitudinal edge of the leg gasketing system pocket.

\* \* \* \* \*